United States Patent
Bilodeau et al.

(10) Patent No.: US 9,556,214 B2
(45) Date of Patent: Jan. 31, 2017

(54) COMPOUNDS, COMPOSITIONS, AND METHODS FOR THE TREATMENT OF CANCERS

(71) Applicant: PLACON THERAPEUTICS, INC., Watertown, MA (US)

(72) Inventors: Mark T. Bilodeau, Concord, MA (US); Craig A. Dunbar, Needham, MA (US); Timothy E. Barder, Arlington, MA (US); Edward R. Lee, Sudbury, MA (US); Rossitza G. Alargova, Brighton, MA (US); Danille N. Rockwood, Medford, MA (US); Rajesh Shinde, Waltham, MA (US); Patrick Lim Soo, Boston, MA (US); Benoît Moreau, Newton, MA (US)

(73) Assignee: PLACON THERAPEUTICS, INC., Watertown, MA (US)

( * ) Notice: Subject to any disclaimer, the term of this patent is extended or adjusted under 35 U.S.C. 154(b) by 0 days.

(21) Appl. No.: 14/654,086

(22) PCT Filed: Dec. 19, 2013

(86) PCT No.: PCT/US2013/076574
§ 371 (c)(1),
(2) Date: Jun. 19, 2015

(87) PCT Pub. No.: WO2014/100417
PCT Pub. Date: Jun. 26, 2014

(65) Prior Publication Data
US 2015/0344511 A1    Dec. 3, 2015

Related U.S. Application Data

(60) Provisional application No. 61/739,234, filed on Dec. 19, 2012.

(51) Int. Cl.
*A61K 31/282* (2006.01)
*C07F 15/00* (2006.01)
*A61K 9/51* (2006.01)

(52) U.S. Cl.
CPC ......... *C07F 15/0093* (2013.01); *A61K 9/5153* (2013.01); *Y10T 428/298* (2015.01)

(58) Field of Classification Search
USPC ................. 514/19.3, 184, 492, 506
See application file for complete search history.

(56) References Cited

U.S. PATENT DOCUMENTS 6,340,770 B1    1/2002 Kwon et al.

FOREIGN PATENT DOCUMENTS

EP    1524273 A1    4/2005

OTHER PUBLICATIONS

Wilson; Inorganic Chemistry, Mar. 1, 2011, 50(7), 3103-3115.*
Wee Han Ang et al: "Synthesis and Characterization of Platinum(IV) Anticancer Drugs with Functionalized Aromatic Carboxylate Ligands: Influence of the Ligands on Drug Efficacies and Uptake", Journal of Medicinal Chemistry, vol. 48, No. 25, Dec. 1, 2005 (Dec. 1, 2005), pp. 8060-8069.
M. Galanski et al: "Carboxylation of Dihydroxoplatinum(IV) Complexes via a New Synthetic Pathway", Inorganic Chemistry, vol. 35, No. 6, Jan. 1, 1996 (Jan. 1, 1996), pp. 1709-1711.
Verena Pichler et al: "Mono-carboxylated diaminedichloridoplatinum(iv) complexes—selective synthesis, characterization, and cytotoxicity", Dalton Transactions, vol. 40, No. 32, Jan. 1, 2011 (Jan. 1, 2011), p. 8187.
Justin J. Wilson et al: "Synthesis, Characterization, and Cytotoxicity of Platinum(IV) Carbamate Complexes", Inorganic Chemistry, vol. 50, No. 7, Apr. 4, 2011 (Apr. 4, 2011), pp. 3103-3115.
Feazell R P et al: "Soluble Single-Walled Carbon Nanotubes as Longboat Delivery Systems for Platinum(IV) Anticancer Drug Desing", Journal of the American Chemical Society, ACS Publications, US, vol. 129, No. 27, Jan. 1, 2007 (Jan. 1, 2007), pp. 8438-8439.
Christen M. Giandomenico et al: "Carboxylation of Kinetically Inert Platinum(IV) Hydroxy Complexes. An Entr. acte.ee into Orally Active Platinum(IV) Antitumor Agents", Inorganic Chemistry, vol. 34, No. 5, Mar. 1, 1995 (Mar. 1, 1995), pp. 1015-1021.
International Search Report, date of mailing Feb. 7, 2014, from International Application No. PCT/US2013/076574, entitled "Compounds, Compositions, and Methods for the Treatment of Cancers," Filing Date: Dec. 19, 2013.

* cited by examiner

*Primary Examiner* — Pancham Bakshi
(74) *Attorney, Agent, or Firm* — DT Ward, PC; Donna T. Ward; Heng Zhu

(57) ABSTRACT

The present teachings relate to compounds and compositions for treatment of cancers. In some embodiments, the composition comprises a platinum (IV) complex having at least one carboxylate or carbamate ligand.

2 Claims, 5 Drawing Sheets

COMPOUNDS, COMPOSITIONS, AND METHODS FOR THE TREATMENT OF CANCERS

FIELD OF THE INVENTION

The invention relates to platinum based compounds and nanoparticle formulations.

BACKGROUND

Platinum-based drugs are among the most active and widely used anticancer agents and cisplatin represents one of the three FDA-approved, platinum-based cancer chemotherapeutics. Although cisplatin is effective against a number of solid tumors, especially testicular and ovarian cancer, its clinical use has been limited because of its toxic effects as well as the intrinsic and acquired resistance of some tumors to this drug.

To overcome these limitations, platinum analogs with lower toxicity and greater activity in cisplatin-resistant tumors have been developed and tested, resulting in the approval of carboplatin and oxaliplatin in the United States. For example, carboplatin has the advantage of being less nephrotoxic, but its cross-resistance with cisplatin has limited its application in otherwise cisplatin-treatable diseases.

Oxaliplatin, however, exhibits a different anticancer spectrum from that of cisplatin. It has been approved as the first or second line therapy in combination with 5-fluorouracil/leucovorin for advanced colorectal cancer, for which cisplatin and carboplatin are essentially inactive. These platinum drugs have platinum in the 2+ oxidative state (Pt(II)) and are not orally active.

Platinum complexes in the 4+ oxidative state (Pt(IV) complexes) provide several advantages. The two additional coordination sites (the axial sites) can be modified to change the pharmacokinetic properties of the complexes. For example, the two axial sites, as well as the four equatorial sites, can include ligands that have one or more lipophilic moieties. In some instances, a Pt(IV) complex having one or more lipophilic moieties can be included in a particle, including a nanoparticle, more efficiently. The lipophilicity increase of and/or the inclusion in a particle of Pt(IV) complexes of the present teachings may increase the Pt concentration in tumor cells. In certain instances, Pt(IV) complexes of the present teachings or nanoparticles of the present teachings including such Pt(IV) complexes can be orally active and/or have a reduced long-term toxicity.

SUMMARY

The present teachings relate to compositions, for example, for reducing, disrupting, or inhibiting the growth of a cancer cell or inducing the death of a cancer cell.

The composition can include a platinum (IV) compound. In various embodiments, the present teachings provide a compound of Formula I:

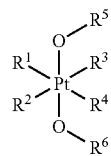

I or a pharmaceutically acceptable salt thereof, wherein:
two of $R^1$, $R^2$, $R^3$, and $R^4$ each independently is a halide;
the remaining two of $R^1$, $R^2$, $R^3$, and $R^4$ each independently is ammonia or an amine; and
$R^5$ and $R^6$ each independently is hydrogen, $R^7$, or

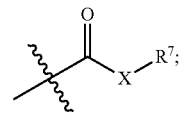

wherein:
X is absent, $C(R^8)_2$, O, S, or $NR^8$, and
$R^7$ and $R^8$ independently at each occurrence is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups optionally is substituted with one or more groups, each independently selected from halogen, cyano, nitro, hydroxyl, ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide, wherein each of the ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide is optionally substituted with one or more suitable substituents.

The present teachings also provide compositions including a compound as described herein and methods of using a compound or a composition as described herein. In various embodiments, the methods of the present teachings are useful for the prevention or treatment of diseases that benefit from increased cell death or decreased cell proliferation. For example, the method of the present teachings can be used to increase cancer cell death or decrease cancer cell proliferation. The increased cancer cell death or decreased cancer proliferation can occur, for example, outside the body (in vitro) or inside the body (in vivo).

Certain embodiments of the present teachings also provide for use of a compound as described herein as a medicament for treating or preventing a disease and/or in the manufacture of such a medicament, e.g., for use in the treatment of a disease. Some embodiments provide the use of a compound as described herein for use as a medicament. In certain embodiments, the teachings provide a compound or composition as described herein for the treatment of disease, e.g. for the treatment of a cancer.

DETAILED DESCRIPTION

Figure 1:
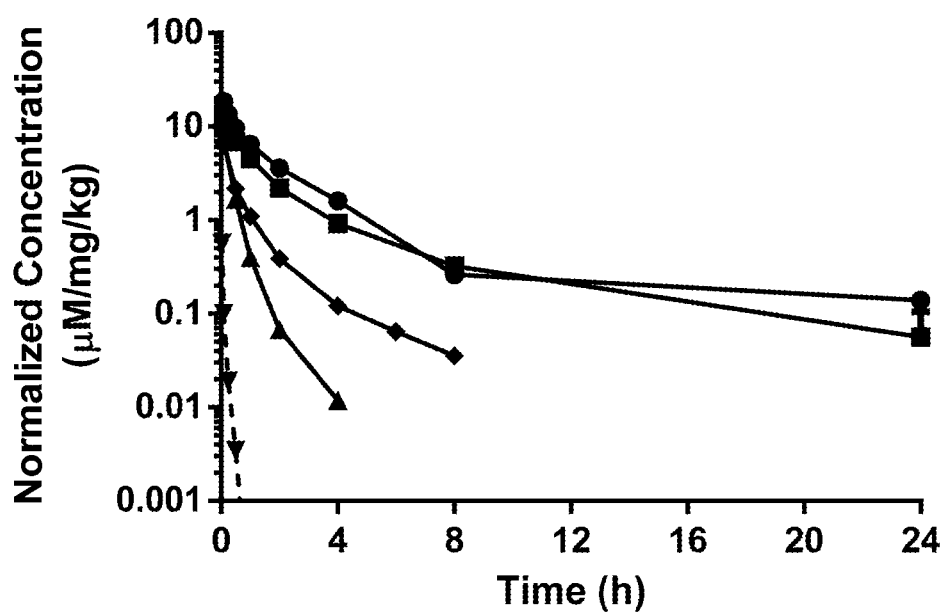
FIG. 1 shows exemplary rat plasma pharmacokinetic (pk) profiles of compound 29 administered as free drug and various exemplary nanoparticles.

For convenience, before further description of the present teachings, certain terms employed in the specification, examples, and appended claims are collected here. These definitions should be read in light of the remainder of the disclosure and as understood by a person of ordinary skill in the art. Unless defined otherwise, all technical and scientific terms used herein have the same meaning as commonly understood by a person of ordinary skill in the art.

The articles "a" and "an," as used herein, should be understood to mean "at least one," unless clearly indicated to the contrary.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements.

In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to.

Only the transitional phrases "consisting of" and "consisting essentially of" shall be closed or semi-closed transitional phrases, respectively, as set forth in the United States Patent Office Manual of Patent Examining Procedures.

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with cancer or otherwise known to have cancer or one selected for treatment, observation, or experiment on the basis of a known cancer in the subject.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

As used herein, "prevention" or "preventing" refers to a reduction of the risk of acquiring a given disease or disorder.

The phrase "therapeutically effective amount" as used herein means that amount of a compound, material, or composition comprising a compound of the present teachings which is effective for producing some desired therapeutic effect. Accordingly, a therapeutically effective amount treats or prevents a disease or a disorder. In various embodiments, the disease or disorder is a cancer.

A dash ("-") that is not between two letters or symbols is used to indicate a point of attachment for a substituent. For example, —$CONH_2$ is attached through the carbon atom (C).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "alkyl" as used herein refers to a saturated straight or branched hydrocarbon, such as a straight or branched group of 1-22, 1-8, 1-6, or 1-4 carbon atoms, referred to herein as ($C_1$-$C_{22}$)alkyl, ($C_1$-$C_8$)alkyl, ($C_1$-$C_6$)

alkyl, and $(C_1-C_4)$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkenyl" as used herein refers to an unsaturated straight or branched hydrocarbon having at least one carbon-carbon double bond (shown, for example, as "="), such as a straight or branched group of 2-22, 2-8, 2-6, or 2-4 carbon atoms, referred to herein as $(C_2-C_{22})$alkenyl, $(C_2-C_8)$alkenyl, $(C_2-C_6)$alkenyl, and $(C_2-C_4)$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkynyl" as used herein refers to an unsaturated straight or branched hydrocarbon having at least one carbon-carbon triple bond (shown, for example, as "≡"), such as a straight or branched group of 2-22, 2-8, 2-6, 2-4 carbon atoms, referred to herein as $(C_2-C_{22})$alkynyl, $(C_2-C_8)$alkynyl, $(C_2-C_6)$alkynyl, and $(C_2-C_4)$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "cycloalkyl" as used herein refers to a saturated or unsaturated monocyclic, bicyclic, other multicyclic, or bridged cyclic hydrocarbon group. A cyclocalkyl group can have 3-22, 3-12, or 3-8 ring carbons, referred to herein as $(C_3-C_{22})$cycloalkyl, $(C_3-C_{12})$cycloalkyl, or $(C_3-C_8)$cycloalkyl, respectively. A cycloalkyl group can also have one or more carbon-carbon double bond or carbon-carbon triple bond.

Exemplary monocyclic cycloalkyl groups include, but are not limited to, cyclopentanes (cyclopentyls), cyclopentenes (cyclopentenyls), cyclohexanes (cyclohexyls), cyclohexenes (cyclopexenyls), cycloheptanes (cycloheptyls), cycloheptenes (cycloheptenyls), cyclooctanes (cyclooctyls), cyclooctenes (cyclooctenyls), cyclononanes (cyclononyls), cyclononenes (cyclononenyls), cyclodecanes (cyclodecyls), cyclodecenes (cyclodecenyls), cycloundecanes (cycloundecyls), cycloundecenes (cycloundecenyls), cyclododecanes (cyclododecyls), and cyclododecenes (cyclododecenyls). Other exemplary cycloalkyl groups, including bicyclic, multicyclic, and bridged cyclic groups, include, but are not limited to, bicyclobutanes (bicyclobutyls), bicyclopentanes (bicyclopentyls), bicyclohexanes (bicyclohexyls), bicycleheptanes (bicycloheptyls, including bicyclo[2,2,1]heptanes (bicycle[2,2,1]heptyls) and bicycle[3,2,0]heptanes (bicycle[3,2,0]heptyls)), bicyclooctanes (bicyclooctyls, including octahydropentalene (octahydropentalenyl), bicycle[3,2,1]octane (bicycle[3,2,1]octyl), and bicylo[2,2,2]octane (bicycle[2,2,2]octyl)), and adamantanes (adamantyls). Cycloalkyl groups can be fused to other cycloalkyl saturated or unsaturated, aryl, or heterocyclyl groups.

The term "aryl" as used herein refers to a mono-, bi-, or other multi-carbocyclic aromatic ring system. The aryl can have 6-22, 6-18, 6-14, or 6-10 carbons, referred to herein as $(C_6-C_{22})$aryl, $(C_6-C_{18})$aryl, $(C_6-C_{14})$aryl, or $(C_6-C_{10})$aryl, respectively. The aryl group can optionally be fused to one or more rings selected from aryls, cycloalkyls, and heterocyclyls. The term "bicyclic aryl" as used herein refers to an aryl group fused to another aromatic or non-aromatic carbocylic or heterocyclic ring. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl" or phenyl. The phenyl group can also be fused to a cyclohexane or cyclopentane ring to form another aryl.

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl." The term "benzyl" as used herein refers to the group —$CH_2$-phenyl.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "heteroalkenyl" and "heteroalkynyl" refer to unsaturated aliphatic groups analogous in length and possible substitution to the heteroalkyls described above, but that contain at least one double or triple bond, respectively.

The term "heterocycle" refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycyclic heterocycle. Thus, heterocycles also include bicyclic, tricyclic, and tetracyclic groups in which any of the above heterocyclic rings is fused to one or two rings independently selected from aryls, cycloalkyls, and heterocycles. The heterocycle may also be fused to a spirocyclic group.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like.

In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, isoquinoline, benzoquinoline, benzoisoquinoline, phenanthridine-1,9-diamine, or the like.

The term "heteroaromatic" or "heteroaryl" as used herein refers to a mono-, bi-, or multi-cyclic aromatic ring system containing one or more heteroatoms, for example 1-3 heteroatoms, such as nitrogen, oxygen, and sulfur. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or stable 12- to 14-membered fused tricyclic heterocyclic ring system which contains an aromatic ring that contains at least one heteroatom selected from the group consisting of N, O, and S. In some embodiments, at least one nitrogen is in the aromatic ring.

Heteroaromatics or heteroaryls can include, but are not limited to, a monocyclic aromatic ring, wherein the ring comprises 2-5 carbon atoms and 1-3 heteroatoms, referred to herein as "($C_2$-$C_5$)heteroaryl." Illustrative examples of monocyclic heteroaromatic (or heteroaryl) include, but are not limited to, pyridine (pyridinyl), pyridazine (pyridazinyl), pyrimidine (pyrimidyl), pyrazine (pyrazyl), triazine (triazinyl), pyrrole (pyrrolyl), pyrazole (pyrazolyl), imidazole (imidazolyl), (1,2,3)- and (1,2,4)-triazole ((1,2,3)- and (1,2,4)-triazolyl), pyrazine (pyrazinyl), pyrimidine (pyrimidinyl), tetrazole (tetrazolyl), furan (furyl), thiophene (thienyl), isoxazole (isoxazolyl), thiazole (thiazolyl), isoxazole (isoxazolyl), and oxazole (oxazolyl).

The term "bicyclic heteroaromatic" or "bicyclic heteroaryl" as used herein refers to a heteroaryl group fused to another aromatic or non-aromatic carbocylic or heterocyclic ring. Exemplary bicyclic heteroaromatics or heteroaryls include, but are not limited to 5,6- or 6,6-fused systems, wherein one or both rings contain heteroatoms. The term "bicyclic heteroaromatic" or "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur.

Exemplary bicyclic heteroaromatics (or heteroaryls) include, but are not limited to, quinazoline (quinazolinyl), benzoxazole (benzoxazolyl), benzothiophene (benzothiophenyl), benzoxazole (benzoxazolyl), benzisoxazole (benzisoxazolyl), benzimidazole (benzimidazolyl), benzothiazole (benzothiazolyl), benzofurane (benzofuranyl), benzisothiazole (benzisothiazolyl), indole (indolyl), indazole (indazolyl), indolizine (indolizinyl), quinoline (quinolinyl), isoquinoline (isoquinolinyl), naphthyridine (naphthyridyl), phthalazine (phthalazinyl), phthalazine (phthalazinyl), pteridine (pteridinyl), purine (purinyl), benzotriazole (benzotriazolyl), and benzofurane (benzofuranyl). In some embodiments, the bicyclic heteroaromatic (or bicyclic heteroaryl) is selected from quinazoline (quinazolinyl), benzimidazole (benzimidazolyl), benzothiazole (benzothiazolyl), indole (indolyl), quinoline (quinolinyl), isoquinoline (isoquinolinyl), and phthalazine (phthalazinyl). In certain embodiments, the bicyclic heteroaromatic (or bicyclic heteroaryl) is quinoline (quinolinyl) or isoquinoline (isoquinolinyl).

The term "tricyclic heteroaromatic" or "tricyclic heteroaryl" as used herein refers to a bicyclic heteroaryl group fused to another aromatic or non-aromatic carbocylic or heterocyclic ring. The term "tricyclic heteroaromatic" or "tricyclic heteroaryl" also refers to reduced or partly reduced forms of fused aromatic system wherein one or both rings contain ring heteroatoms. Each of the ring in the tricyclic heteroaromatic (tricyclic heteroaryl) may contain up to three heteroatoms, independently selected from oxygen, nitrogen, and sulfur.

Exemplary tricyclic heteroaromatics (or heteroaryls) include, but are not limited to, acridine (acridinyl), 9H-pyrido[3,4-b]indole (9H-pyrido[3,4-b]indolyl), phenanthridine (phenanthridinyl), pyrido[1,2-a]benzimidazole (pyrido[1,2-a]benzimidazolyl), and pyrido[1,2-b]indazole (pyrido[1,2-b]indazolyl).

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as ($C_1$-$C_{22}$)alkoxy, ($C_1$-$C_8$)alkoxy, or ($C_1$-$C_6$)alkoxy, respectively. Exemplary alkoxy groups include, but are not limited to methoxy and ethoxy.

The term "cycloalkoxy" as used herein refers to a cycloalkyl group attached to an oxygen.

The term "aryloxy" or "aroxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "($C_6$)aryloxy."

The term "arylalkoxy" as used herein refers to an arylalkyl group attached to an oxygen atom. An exemplary aryalkyl group is benzyloxy group.

The term "amine" or "amino" as used herein refers to both unsubstituted and substituted amines, e.g., $NR_aR_bR_{b'}$, where $R_a$, $R_b$, and $R_{b'}$ are independently selected from alkyl, alkenyl, alkynyl, aryl, arylalkyl, carbamate, cycloalkyl, haloalkyl, heteroaryl, heterocyclyl, and hydrogen, and at least one of the $R_a$, $R_b$, and $R_{b'}$ is not hydrogen. The amine or amino can be attached to the parent molecular group through the nitrogen. The amine or amino also may be cyclic, for example any two of $R_a$, $R_b$, and $R_{b'}$ may be joined together and/or with the N to form a 3- to 12-membered ring (e.g., morpholino or piperidinyl). The term amino also includes the corresponding quaternary ammonium salt of any amino group. Exemplary amines include alkylamine, wherein at least one of $R_a$ $R_b$, or $R_{b'}$ is an alkyl group, or cycloalkylamine, wherein at least one of $R_aR_b$, or $R_{b'}$ is a cycloalkyl group.

The term "ammonia" as used herein refers to $NH_3$.

The term "aldehyde" or "formyl" as used herein refers to —CHO.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "amide" as used herein refers to the form —$NR_cC(O)(R_d)$— or —$C(O)NR_cR_e$, wherein $R_c$, $R_d$, and $R_e$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_c$, $R_d$, or $R_e$. The amide also may be cyclic, for example $R_c$ and $R_e$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa.

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "($C_6$)arylthio."

The term "arylsulfonyl" as used herein refers to an aryl group attached to a sulfonyl group, e.g., —S(O)$_2$-aryl-. Exemplary arylsulfonyl groups include, but are not limited to, arylsulfonyls having a monocyclic aromatic ring system, wherein the ring comprises 6 carbon atoms, referred to herein as "($C_6$)arylsulfonyl."

The term "carbamate" as used herein refers to the form —R$_f$OC(O)N(R$_g$)—, —R$_f$OC(O)N(R$_g$)R$_h$—, or —OC(O)NR$_g$R$_h$, wherein R$_f$, R$_g$, and R$_h$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of R$_f$, R$_g$ and R$_h$ are independently selected from aryl or heteroaryl, such as pyridinyl, pyridazinyl, pyrimidinyl, and pyrazinyl).

The term "carbonyl" as used herein refers to —C(O)—.

The term "carboxy" or "carboxylate" as used herein refers to R$_j$—COOH or its corresponding carboxylate salts (e.g., R$_j$—COONa), where R$_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. Exemplary carboxys include, but are not limited to, alkyl carboxy wherein R$_j$ is alkyl, such as —O—C(O)-alkyl. Exemplary carboxy also include aryl or heteroaryl carboxy, e.g. wherein R$_j$ is an aryl, such as phenyl and tolyl, or heteroaryl group such as pyridine, pyridazine, pyrimidine and pyrazine. The term carboxy also includes "carboxycarbonyl," e.g. a carboxy group attached to a carbonyl group, e.g., —C(O)—COOH or salts, such as —C(O)—COONa.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "cyano" as used herein refers to —CN.

The term "ester" refers to the structure —C(O)O—, —C(O)O—R$_i$—, —R$_j$C(O)O—R$_i$—, or —R$_j$C(O)O—, where O is not bound to hydrogen, and R$_i$ and R$_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. R$_i$ can be a hydrogen, but R$_j$ cannot be hydrogen. The ester may be cyclic, for example the carbon atom and R$_j$, the oxygen atom and R$_i$, or R$_i$ and R$_j$ may be joined to form a 3- to 12-membered ring. Exemplary esters include, but are not limited to, alkyl esters wherein at least one of R$_i$ or R$_j$ is alkyl, such as —O—C(O)-alkyl, —C(O)—O-alkyl, and -alkyl-C(O)—O-alkyl-. Exemplary esters also include aryl or heteroaryl esters, e.g. wherein at least one of R$_i$ or R$_j$ is an aryl group, such as phenyl or tolyl, or a heteroaryl group, such as pyridine, pyridazine, pyrimidine or pyrazine, such as a nicotinate ester. Exemplary esters also include reverse esters having the structure —R$_j$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —R$_k$O—R$_l$—, where R$_k$ and R$_l$ can independently be alkyl, alkenyl, alkynyl, aryl, cycloalkyl, heterocyclyl, and ether. The ether can be attached to the parent molecular group through R$_k$ or R$_l$. Exemplary ethers include, but are not limited to, alkoxyalkyl and alkoxyaryl groups. Ethers also includes polyethers, e.g., where one or both of R$_k$ and R$_l$ are ethers.

The terms "halo" or "halogen" or "hal" or "halide" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—R$_n$ (such as acetyl, —C(O)CH$_3$) or —R$_m$C(O)—R$_n$—. The ketone can be attached to another group through R$_m$ or R$_n$. R$_m$ or R$_n$ can be alkyl, alkenyl, alkynyl, cycloalkyl, heterocyclyl or aryl, or R$_m$ or R$_n$ can be joined to form, for example, a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —NO$_2$.

The term "nitrate" as used herein refers to NO$_3$.

The term "perfluoroalkyl" as used herein refers to an alkyl group in which all of the hydrogen atoms have been replaced by fluorine atoms. Exemplary perfluoroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "perfluoroalkoxy" as used herein refers to an alkoxy group in which all of the hydrogen atoms have been replaced by fluorine atoms.

The term "phosphate" as used herein refers to the structure —OP(O)O$_2^{2-}$, —R$_o$OP(O)O$_2^{2-}$, —OP(O)(OR$_q$)O$^-$, or —R$_o$OP(O)(OR$_p$)O$^-$, wherein R$_o$, R$_p$ and R$_q$ each independently can be alkyl, alkenyl, alkynyl, aryl, cycloalkyl, heterocyclyl, or hydrogen.

The term "sulfide" as used herein refers to the structure —R$_q$S—, where R$_q$ can be alkyl, alkenyl, alkynyl, aryl, arylalkyl, cycloalkyl, haloalkyl, heteroaryl, heterocyclyl. The sulfide may be cyclic, for example, forming a 3 to 12-membered ring. The term "alkylsulfide" as used herein refers to an alkyl group attached to a sulfur atom.

The term "sulfinyl" as used herein refers to the structure —S(O)O—, —R$_r$S(O)O—, —R$_r$S(O)OR$_s$—, or —S(O)OR$_s$, wherein R$_r$ and R$_s$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of $R_r$ or $R_s$ is alkyl, alkenyl, or alkynyl.

The term "sulfonamide" as used herein refers to the structure —$(R_t)$—N—S(O)$_2$—$R_v$— or —$R_t(R_u)$N—S(O)$_2$—$R_v$, where $R_t$, $R_u$, and $R_v$ can be, for example, hydrogen, alkyl, alkenyl, alkynyl, aryl, cycloalkyl, and heterocyclyl. Exemplary sulfonamides include alkylsulfonamides (e.g., where $R_v$ is alkyl), arylsulfonamides (e.g., where $R_v$ is aryl), cycloalkyl sulfonamides (e.g., where $R_v$ is cycloalkyl), and heterocyclyl sulfonamides (e.g., where $R_v$ is heterocyclyl).

The term "sulfonate" as used herein refers to a salt or ester of a sulfonic acid. The term "sulfonic acid" refers to $R_w SO_3 H$, where $R_w$ is alkyl, alkenyl, alkynyl, aryl, cycloalkyl, or heterocyclyl (e.g., alkylsulfonyl). The term "sulfonyl" as used herein refers to the structure $R_x$—SO$_2$—, where $R_x$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "sulfonate" as used herein refers $R_w SO_3^-$, where $R_w$ is alkyl, alkenyl, alkynyl, cycloalkyl, aryl, heterocyclyl, hydroxyl, alkoxy, aroxy, or aralkoxy, where each of the alkyl, alkenyl, alkynyl, cycloalkyl, aryl, heteroaryl, alkoxy, aroxy, or aralkoxy optionally is substituted. Non-limiting examples include triflate (also known as trifluoromethanesulfonate, $CF_3 SO_3^-$), benzenesulfonate, tosylate (also known as toluenesulfonate), and the like.

The term "thioketone" refers to the structure —$R_y$—C(S)—$R_z$—. The ketone can be attached to another group through $R_y$ or $R_z$. $R_y$ or $R_z$ can be alkyl, alkenyl, alkynyl, cycloalkyl, heterocyclyl or aryl, or $R_y$ or $R_z$ can be joined to form a ring, for example, a 3- to 12-membered ring.

Each of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of the present teachings, the heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

As a non-limiting example, in various embodiments when one of the $R_a$, $R_b$, and $R_{b'}$ in $NR_a R_b R_{b'}$, referred to herein as an amine or amino, is selected from alkyl, alkenyl, alkynyl, cycloalkyl, and heterocyclyl, each of the alkyl, alkenyl, alkynyl, cycloalkyl, and heterocyclyl independently can be optionally substituted with one or more substituents each independently selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents. In some embodiments when the amine is an alkyl amine or a cycloalkylamine, the alkyl or the cycloalkyl can be substituted with one or more substituents each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. In certain embodiments when the amine is an alkyl amine or a cycloalkylamine, the alkyl or the cycloalkyl can be substituted with one or more substituents each independently selected from amino, carboxy, cyano, and hydroxyl. For example, the alkyl or the cycloalkyl in the alkyl amine or the cycloalkylamine is substituted with an amino group, forming a diamine.

As used herein, a "suitable substituent" refers to a group that does not nullify the synthetic or pharmaceutical utility of the compounds of the invention or the intermediates useful for preparing them. Examples of suitable substituents include, but are not limited to: ($C_1$-$C_{22}$), ($C_1$-$C_8$), ($C_1$-$C_6$), or ($C_1$-$C_4$) alkyl, alkenyl or alkynyl; ($C_6$-$C_{22}$), ($C_6$-$C_{18}$), ($C_6$-$C_{14}$), or ($C_6$-$C_{10}$) aryl; ($C_2$-$C_{21}$), ($C_2$-$C_{17}$), ($C_2$-$C_{13}$), or ($C_2$-$C_9$) heteroaryl; ($C_3$-$C_{22}$), ($C_3$-$C_{12}$), or ($C_3$-$C_8$) cycloalkyl; ($C_1$-$C_{22}$), ($C_1$-$C_8$), ($C_1$-$C_6$), or ($C_1$-$C_4$) alkoxy; ($C_6$-$C_{22}$), ($C_6$-$C_{18}$), ($C_6$-$C_{14}$), or ($C_6$-$C_{10}$) aryloxy; —CN; —OH; oxo; halo; carboxy; amino, such as —NH(($C_1$-$C_{22}$), ($C_1$-$C_8$), ($C_1$-$C_6$), or ($C_1$-$C_4$) alkyl), —N(($C_1$-$C_{22}$), ($C_1$-$C_8$), ($C_1$-$C_6$), or ($C_1$-$C_4$) alkyl)$_2$, —NH(($C_6$)aryl), or —N(($C_6$-$C_{10}$) aryl)$_2$; formyl; ketones, such as —CO(($C_1$-$C_{22}$), ($C_1$-$C_8$), ($C_1$-$C_6$), or ($C_1$-$C_4$) alkyl), —CO((($C_6$-$C_{10}$) aryl) esters, such as —$CO_2$(($C_1$-$C_{22}$), ($C_1$-$C_8$), ($C_1$-$C_6$), or ($C_1$-$C_4$) alkyl) and —$CO_2$(($C_6$-$C_{10}$) aryl). One of skill in art can readily choose a suitable substituent based on the stability and pharmacological and synthetic activity of the compound of the invention.

The term "pharmaceutically acceptable counter ion" refers to a pharmaceutically acceptable anion or cation. In various embodiments, the pharmaceutically acceptable counter ion is a pharmaceutically acceptable ion. For example, the pharmaceutically acceptable counter ion is selected from citrate, matate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). In some embodiments, the pharmaceutically acceptable counter ion is selected from chloride, bromide, iodide, nitrate, sulfate, bisulfate, phosphate, acid phosphate, citrate, matate, acetate, oxalate, acetate, and lactate. In particular embodiments, the pharmaceutically acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present teachings. Compounds included in the present teachings that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present teachings that include an amino moiety may form pharmaceutically acceptable salts with various amino acids, in addition to the acids mentioned above. Compounds included in the present teachings, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

Unless otherwise specified, the chemical groups include their corresponding monovalent, divalent, trivalent, and tetravalent groups. For example, methyl includes monovalent methyl (—$CH_3$), divalent methyl (—$CH_2$—, methylyl), trivalent methyl

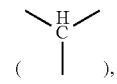

and tetravalent methyl

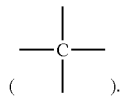

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques. For example, the term "about" can encompass variations of ±10%, ±5%, ±2%, ±1%, ±0.5%, or ±0.1% of the numerical value of the number which the term "about" modifies. In various embodiments, the term "about" encompasses variations of ±5%, ±2%, ±1%, or ±0.5% of the numerical value of the number. In some embodiments, the term "about" encompasses variations of ±5%, ±2%, or ±1% of the numerical value of the number. In certain embodiments, the term "about" encompasses variations of ±5% of the numerical value of the number. In certain embodiments, the term "about" encompasses variations of ±2% of the numerical value of the number. In certain embodiments, the term "about" encompasses variations of ±1% of the numerical value of the number.

All numerical ranges herein include all numerical values and ranges of all numerical values within the recited range of numerical values. As a non-limiting example, $(C_1-C_6)$ alkyls also include any one of $C_1$, $C_2$, $C_3$, $C_4$, $C_5$, $C_6$, $(C_1-C_2)$, $(C_1-C_3)$, $(C_1-C_4)$, $(C_1-C_5)$, $(C_2-C_3)$, $(C_2-C_4)$, $(C_2-C_5)$, $(C_2-C_6)$, $(C_3-C_4)$, $(C_3-C_5)$, $(C_3-C_6)$, $(C_4-C_5)$, $(C_4-C_6)$, and $(C_5-C_6)$ alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

A "polymer," as used herein, is given its ordinary meaning as used in the art, i.e., a molecular structure comprising one or more repeating units (monomers), connected by covalent bonds. The repeating units may all be identical, or in some cases, there may be more than one type of repeating unit present within the polymer.

If more than one type of repeating unit is present within the polymer, then the polymer is said to be a "copolymer." It is to be understood that in any embodiment employing a polymer, the polymer being employed may be a copolymer in some cases. The repeating units forming the copolymer may be arranged in any fashion. For example, the repeating units may be arranged in a random order, in an alternating order, or as a "block" copolymer, i.e., comprising one or more regions each comprising a first repeating unit (e.g., a first block), and one or more regions each comprising a second repeating unit (e.g., a second block), etc. Block copolymers may have two (a diblock copolymer), three (a triblock copolymer), or more numbers of distinct blocks.

The term "hydrophilic," as used herein, generally describes the property of attracting water and the term "hydrophobic," as used herein, generally describes the property of repelling water. Thus, a hydrophilic compound (e.g., small molecule or polymer) is one generally that attracts water and a hydrophobic compound (e.g., small molecule or polymer) is one that generally repels water. A hydrophilic or a hydrophobic compound can be identified, for example, by preparing a sample of the compound and measuring its contact angle with water. In some cases, the hydrophilicity of two or more compounds may be measured relative to each other, i.e., a first compound may be more hydrophilic than a second compound.

The present teachings generally provide compounds, compositions, and methods of using the compounds or compositions.

In various embodiments, each of the compounds of the present teachings has Formula I:

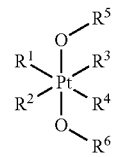

I or a pharmaceutically acceptable salt thereof,
wherein:
two of $R^1$, $R^2$, $R^3$, and $R^4$ each independently is a halide;
the remaining two of $R^1$, $R^2$, $R^3$, and $R^4$ each independently is ammonia or an amine; and
$R^5$ and $R^6$ each independently is hydrogen, $R^7$, or

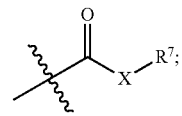

wherein:
X is absent, $C(R^8)_2$, O, S, or $NR^8$, and
$R^7$ and $R^8$ at each occurrence independently is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups optionally is substituted with one or more groups, each independently selected from halogen, cyano, nitro, hydroxyl, ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide, wherein each of the ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide is optionally substituted with one or more suitable substituents.

In some embodiments, the compound is not ethacraplatin, cis,cis,trans-[Pt(NH$_3$)$_2$Cl$_2$(OH)$_2$], cis,cis,trans-[Pt(NH$_2$(isopropyl))$_2$Cl$_2$(OH)$_2$], cis,cis,trans-[Pt(NH$_3$)$_2$Cl$_2$(O$_2$C(CH$_2$)$_4$CH$_3$)$_2$], cis,cis,trans-[Pt(NH$_3$)$_2$Cl$_2$(O$_2$C(CH$_2$)$_2$CO$_2$H)$_2$], cis,cis,trans-[Pt(NH$_3$)$_2$Cl$_2$(O$_2$CCF$_3$)$_2$], cis,cis,trans-[Pt(NH$_3$)$_2$Cl$_2$(O$_2$CCHCl$_2$)$_2$], cis,cis,trans-[Pt(NH$_3$)$_2$Cl$_2$(O$_2$CCH$_3$)$_2$], cis,cis,trans-[PtNH$_3$(NH$_2$(isopropyl))Cl$_2$(O$_2$CCH$_3$)$_2$], cis,cis,trans-[PtNH$_3$(NH$_2$(cyclohexyl))Cl$_2$(O$_2$CCH$_3$)$_2$], cis,cis,trans-[PtNH$_3$(NH$_2$(adamantyl))Cl$_2$(O$_2$CCH$_3$)$_2$], cis,cis,trans-[PtNH$_3$(NH$_2$(cyclohexyl))Cl$_2$(O$_2$C(CH$_2$)$_5$CH$_3$)$_2$], cis,cis,trans-[Pt(NH$_3$)$_2$Cl$_2$(O$_2$CNHC(CH$_3$)$_3$)$_2$], cis,cis,trans-[Pt(NH$_3$)$_2$Cl$_2$(O$_2$CNH(cyclopentyl))$_2$], or cis,cis,trans-[Pt(NH$_3$)$_2$Cl$_2$(O$_2$CNH(cyclohexyl))$_2$].

In various embodiments, the compound is lipophilic. In some embodiments, at least one of $R^1$, $R^2$, $R^3$, $R^4$, $R^5$, and $R^6$ comprises a lipophilic moiety. In certain embodiments, at least two of $R^1$, $R^2$, $R^3$, $R^4$, $R^5$, and $R^6$ each comprises a lipophilic moiety. In particular embodiments, two of $R^1$, $R^2$, $R^3$, and $R^4$ each comprise a lipophilic moiety. For example, two of $R^1$, $R^2$, $R^3$, and $R^4$, joined together, can comprise a lipophilic moiety. In particular embodiments, at least one of $R^5$ and $R^6$ comprises a lipophilic moiety. For example, each of $R^5$ and $R^6$ can comprise a lipophilic moiety. A lipophilic moiety in various embodiments can be alkyl, alkenyl, alkynyl, cycloalkyl, heterocyclyl, aryl, or heteroaryl, each of which is optionally substituted with one or more suitable substituents.

In various embodiments, at least one of $R^1$, $R^2$, $R^3$, and $R^4$ is a halide. For example, at least one of $R^1$, $R^2$, $R^3$, and $R^4$ is Cl. In some embodiments, two of $R^1$, $R^2$, $R^3$, and $R^4$ each is a halide. In some embodiments, two of $R^1$, $R^2$, $R^3$, and $R^4$ each is Cl.

In various embodiments, at least one of $R^1$, $R^2$, $R^3$, and $R^4$ is ammonia. In some embodiments, two of $R^1$, $R^2$, $R^3$, and $R^4$ each is ammonia.

In various embodiments, at least one of $R^1$, $R^2$, $R^3$, and $R^4$ is an amine. In some embodiments, two of $R^1$, $R^2$, $R^3$, and $R^4$ each is an amine. In some embodiments, two of $R^1$, $R^2$, $R^3$, and $R^4$ form a bidentate ligand as described herein.

Some embodiments comprise compounds having two ligands (e.g., $R^1$, $R^2$, $R^3$, and $R^4$) positioned in a cis configuration, i.e., the compound may be a cis isomer. However, it should be understood that compounds of the present teachings may also have two ligands (e.g., $R^1$, $R^2$, $R^3$, and $R^4$) positioned in a trans configuration, i.e., the compound may be a trans isomer. Those of ordinary skill in the art would understand the meaning of these terms.

In various embodiments, the compounds of the present teachings each has Formula Ia:

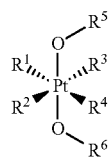

Ia wherein $R^1$, $R^2$, $R^3$, $R^4$, $R^5$, and $R^6$ are as defined herein.

In some embodiments, at least one of $R^3$ and $R^4$ is a halide. In certain embodiments, both $R^3$ and $R^4$ are Cl.

In some embodiments, at least one of $R^1$ and $R^2$ is ammonia. In certain embodiments, both $R^1$ and $R^2$ are ammonia.

In some embodiments, at least one of $R^1$ and $R^2$ is an amine. For example, at least one of $R^1$ and $R^2$ is an alkylamine, alkenylamine, alkynylamine, arylamine, arylalkylamine, cycloalkylamine, heterocycloalkylamine, or heteroarylamine. In certain embodiments, one of $R^1$ and $R^2$ is methylamine, ethylamine, propylamine, isopropylamine, butylamine, isobutylamine, tertbutylamine, cyclopentylamine, cyclohexylamine, or adamantylamine. In certain embodiments, $R^1$ and $R^2$ form a bidentate ligand as described herein.

In various embodiments, the compounds of the present teachings each has Formula IIa:

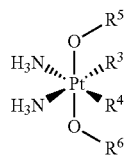

IIa wherein $R^3$, $R^4$, $R^5$, and $R^6$ are as defined herein.

In some embodiments, two ligands may be joined together to form a bidentate ligand. As will be known to those of ordinary skill in the art, a bidentate ligand, as used herein, when bound to a metal center, forms a metallacycle structure with the metal center, also known as a chelate ring. Bidentate ligands include species that have at least two sites capable of binding to a metal center. For example, a bidentate ligand may comprise at least two heteroatoms that coordinate the metal center, or a heteroatom and an anionic carbon atom that coordinate the metal center.

Examples of bidentate ligands suitable for use in the present teachings include diamines, including ethylenediamine, cyclohexyldiamine, cyclobutanediyldimethanamine, and the like. In some embodiments, $R^1$ and $R^2$ joined together form ethylenediamine, cyclobutane-1,2-diyldimethanamine, cyclohexane-1,2-diamine, or the like. In certain embodiments, $R^1$ and $R^2$ joined together form cyclobutane-1,2-diyldimethanamine or cyclohexane-1,2-diamine. In certain embodiments, $R^1$ and $R^2$ joined together form cyclohexane-1,2-diamine.

In various embodiments, the compounds of the present teachings each has Formula IIb:

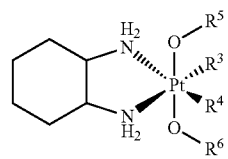

IIb wherein $R^3$, $R^4$, $R^5$, and $R^6$ are as defined herein.

Without limiting the scope of the present teachings, in some embodiments, $R^1$ and $R^2$ joined together and forming ethylenediamine, cyclobutane-1,2-diyldimethanamine or cyclohexane-1,2-diamine increases the lipophilicity of the compounds of the present teachings.

In various embodiments, one of $R^5$ and $R^6$ is hydrogen. In various embodiments, at least one of $R^5$ and $R^6$ is $R^7$. For example, $R^5$ can be hydrogen and $R^6$ can be $R^7$ or $R^6$ can be hydrogen and $R^5$ can be $R^7$. In some embodiments, both $R^5$ and $R^6$ are $R^7$.

In various embodiments, at least one of $R^5$ and $R^6$ is

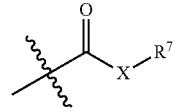

For example, $R^5$ can be hydrogen and $R^6$ can be

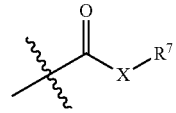

or $R^6$ can be hydrogen and $R^5$ can be

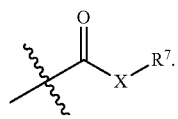

In some embodiments, both $R^5$ and $R^6$ are

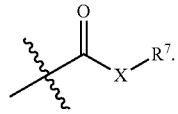

In various embodiments, X is absent.

In various embodiments, X is $C(R^8)_2$, wherein each $R^8$ independently is defined herein. In various embodiments, X is $NR^8$, where $R^8$ is as defined herein.

In various embodiments, $R^8$ at each occurrence is hydrogen or alkyl, optionally substituted with one or more groups, each independently selected from halogen, cyano, nitro, ester, ether, alkoxy, aryloxy, amide, carbamate, alkenyl, alkynyl, aryl, arylalkyl, cycloalkyl, heteroaryl, and heterocyclyl, wherein each of the ester, ether, alkoxy, aryloxy, amide, carbamate, alkenyl, alkynyl, aryl, arylalkyl, cycloalkyl, heteroaryl, and heterocyclyl is optionally substituted with one or more suitable substituents. In some embodiments, $R^8$ at least at one occurrence is hydrogen. In some embodiments, $R^8$ at least at one occurrence is an optionally substituted alkyl. For example, $R^8$ at least at one occurrence is an alkyl (e.g., methyl, ethyl, propyl, or isopropyl).

In particular embodiments, X is $CH_2$ or $C(CH_3)_2$. In particular embodiments, X is NH.

In various embodiments, $R^7$ is alkyl or cycloalkyl. For example, $R^7$ is alkyl optionally substituted with one or more groups each independently selected from halogen, hydroxyl, ester, alkoxy, aryloxy, amino, amide, aryl, arylalkyl, cycloalkyl, heteroaryl, and heterocyclyl, wherein each of ester, alkoxy, aryloxy, amino, amide, aryl, arylalkyl, cycloalkyl, heteroaryl, and heterocyclyl optionally is substituted with one or more suitable substituents. In some embodiments, $R^7$ is alkyl optionally substituted with one or more groups each independently selected from halogen, hydroxyl, alkoxy, aryloxy, arylalkoxy, amino, amide, and aryl, wherein each of the alkoxy, aryloxy, arylalkoxy, amino, amide, and aryl optionally is substituted with one or more substituents, each independently selected from one or more suitable substituents. In certain embodiments, $R^7$ is alkyl optionally substituted with one or more groups each independently selected from F, Cl, phenyl, benzyloxy, t-butylphenyl, amino, and bistrifluoromethylphenyl. For example, $R^7$ is a $(C_1-C_{22})$alkyl. In particular embodiments, $R^7$ is benzyl. In particular embodiments, $R^7$ is butyl, tert-butyl, pentyl, heptyl, octyl, nonyl, undecyl, dodecanyl, tridecyl, heptadecyl, 1,1,3,3-tetramethylbutyl, 2-ethylhexyl, 2,2-dimethylpropyl, 2,2,3,3,4,4,4-heptafluorobutyl, 2,2,3,3,4,4,5,5,5-nonafluoropentyl, aminomethyl, tert-butoxycarbonylaminomethyl, hydroxylcarbonylmethyl, diphenylmethyl, 4'-t-butylbenzyl, 2-benzyloxylethyl, 1-adamantylmethyl, or 3',5'-ditrifluoromethylbenzyl.

In various embodiments, $R^7$ is cycloalkyl. For example, $R^7$ can be monocyclic, bicyclic, or bridged cyclic cycloalkyl having 3-14 ring carbons. In some embodiments, $R^7$ is cycloalkyl optionally substituted with one or more groups each independently selected from halogen, hydroxyl, ester, alkoxy, aryloxy, amino, amide, alkyl, alkenyl, alkynyl, aryl, arylalkyl, cycloalkyl, heteroaryl, and heterocyclyl, wherein each of ester, alkoxy, aryloxy, amino, amide, alkyl, alkenyl, alkynyl, aryl, arylalkyl, cycloalkyl, heteroaryl, and heterocyclyl optionally is substituted with one or more suitable substituents. For example, $R^7$ can be cycloalkyl optionally substituted with one or more groups each independently selected from halogen, hydroxyl, alkoxy, aryloxy, arylalkoxy, amino, amide, alkyl, alkenyl, and aryl, wherein each of alkoxy, aryloxy, arylalkoxy, amino, amide, alkyl, alkenyl, and aryl optionally is substituted with one or more substituents, each independently selected from one or more suitable substituents.

In certain embodiments, $R^7$ is selected from cyclohexyl, cycloheptyl, cyclooctyl, cyclopentyl, cyclodecanyl, cycloundecanyl, cyclododecanyl, camphanyl, camphenyl, or adamantyl. In particular embodiments, $R^7$ is cyclohexyl, cyclododecanyl, or adamantyl.

In various embodiments, $R^7$ at each occurrence is selected from aryl and heteroaryl, wherein each of the aryl and heteroaryl groups optionally is substituted with one or more groups, each independently selected from halogen, cyano, nitro, hydroxyl, ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide, wherein each of the ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide is optionally substituted with one or more suitable substituents. In some embodiments, $R^7$ at each occurrence is aryl optionally substituted with one or more groups, each independently selected from halogen, cyano, nitro, hydroxyl, ester, ether, alkoxy, aryloxy, amino, amide, carbamate, alkyl, alkenyl, alkynyl, aryl, arylalkyl, cycloalkyl, heteroaryl, and heterocyclyl, wherein each of the ester, ether, alkoxy, aryloxy, amino, amide, carbamate, alkyl, alkenyl, alkynyl, aryl, arylalkyl, cycloalkyl, heteroaryl, and heterocyclyl is optionally substituted with one or more suitable substituents. For example, $R^7$ is aryl optionally substituted with one or more groups, each independently selected from halogen, cyano, nitro, hydroxyl, ester, ether, alkoxy, aryloxy, amino, amide, alkyl, aryl, arylalkyl, cycloalkyl, heteroaryl, and heterocyclyl. In certain embodiments, $R^7$ is phenyl optionally substituted with one or more groups, each independently selected from halogen, cyano, nitro, hydroxyl, ester, ether, alkoxy, aryloxy, amino, amide, alkyl, aryl, arylalkyl, cycloalkyl, heteroaryl, and heterocyclyl. In particular embodiments, $R^7$ is phenyl or 2,4-dimethylphenyl.

In various embodiments, $R^5$ and $R^6$ are different. For example, the compound of the present teachings can be selected from:

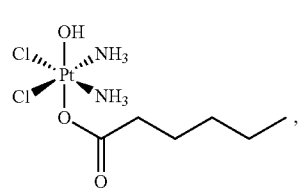

1

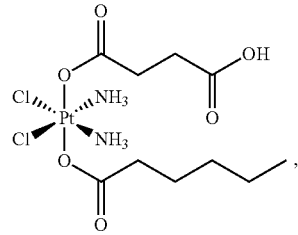

2

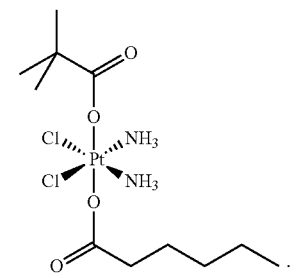

3

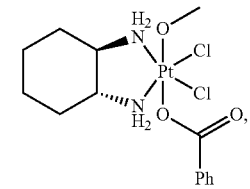

4

-continued
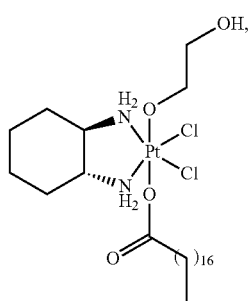
5
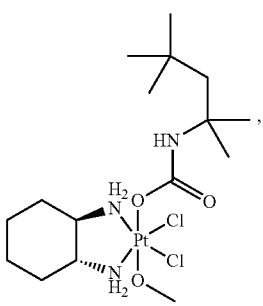
6
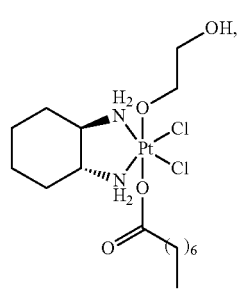
7
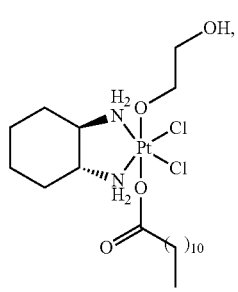
8
-continued
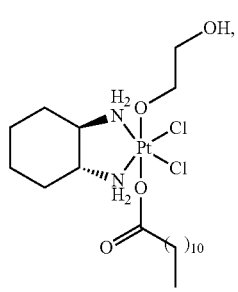
9
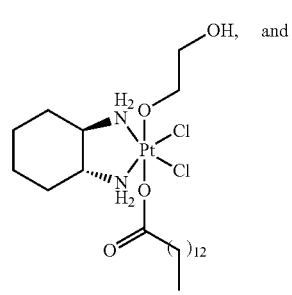
10
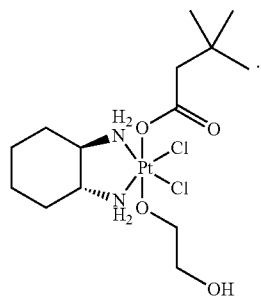
11
In various embodiments, $R^5$ and $R^6$ can be the same. For example, the compound of the present teachings can be selected from:
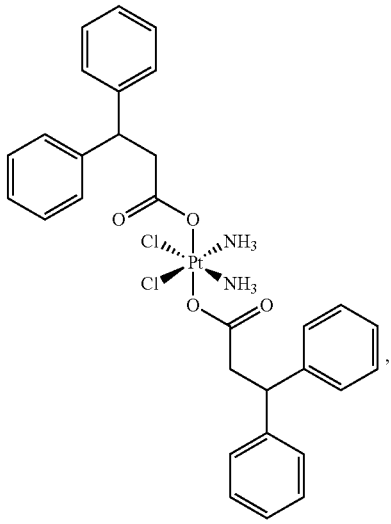
12

23
-continued
13
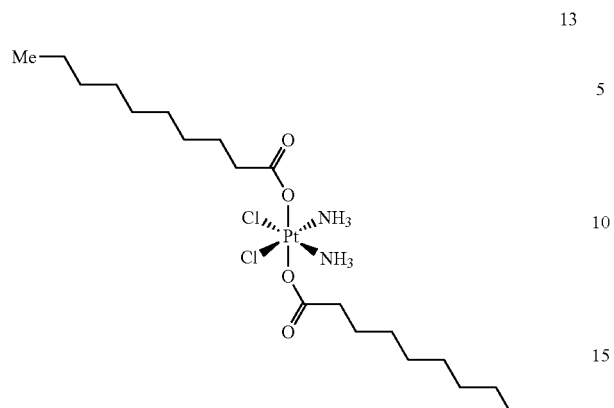
14
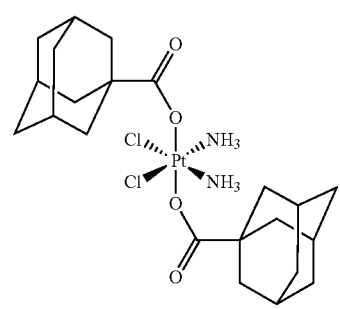
15
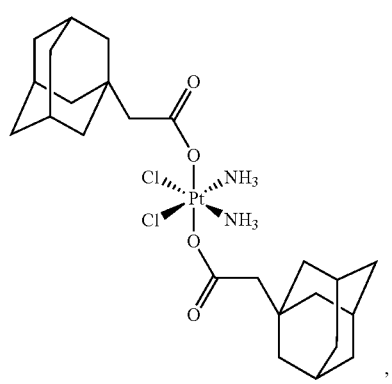
16
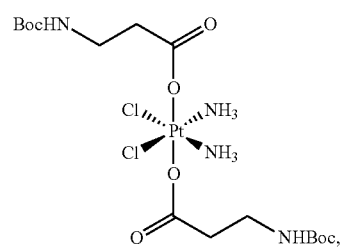
17
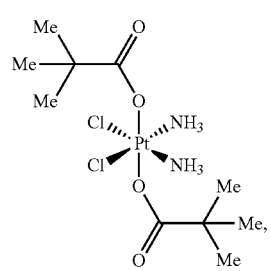
24
-continued
18
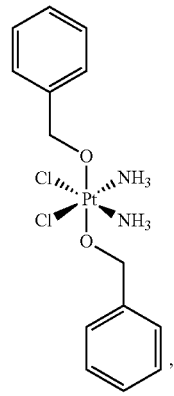
19
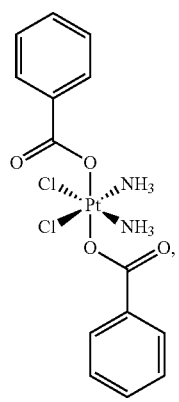
20
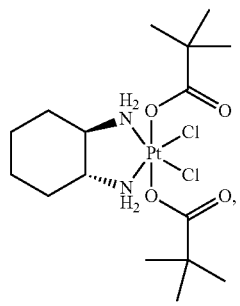
21
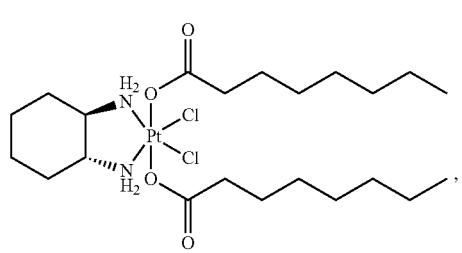
22
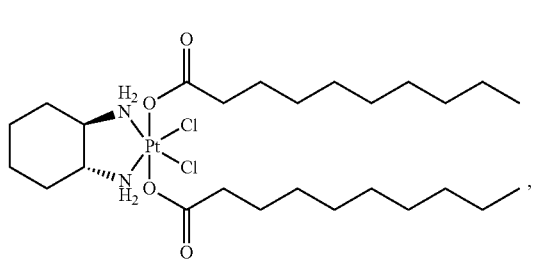

23
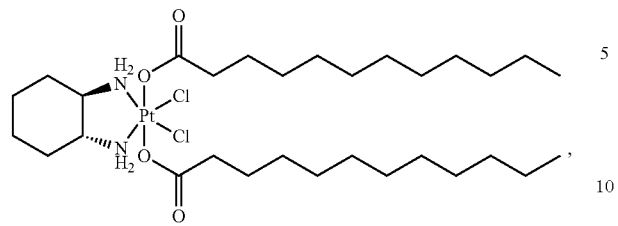
24
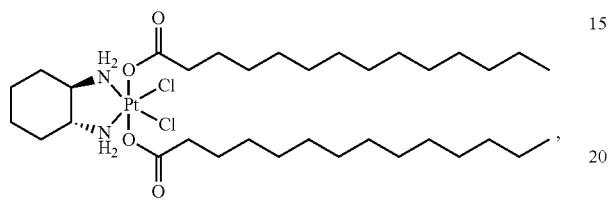
25
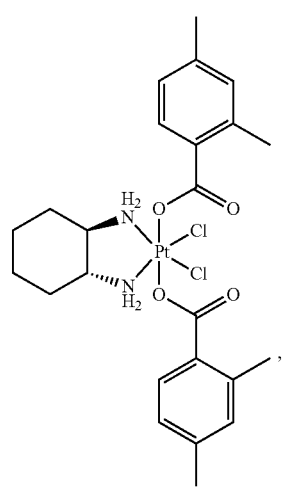
26
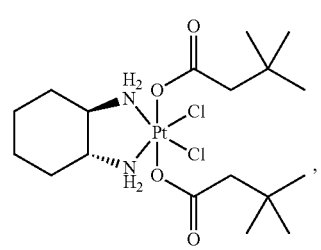
27
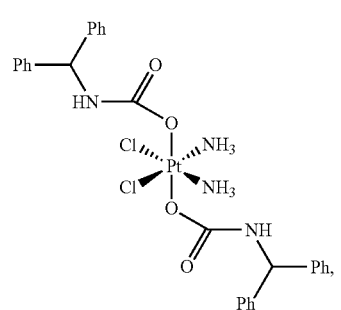
28
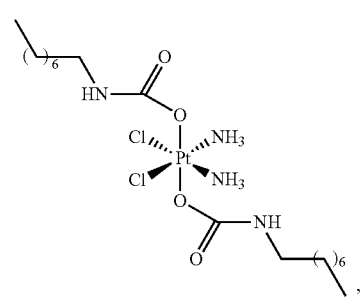
29
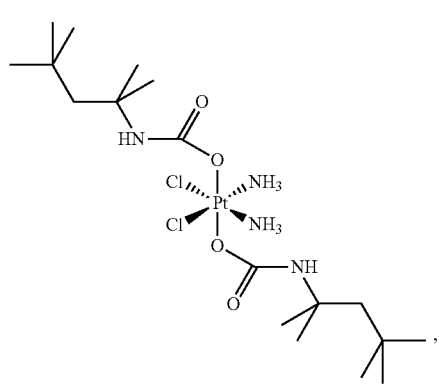
30
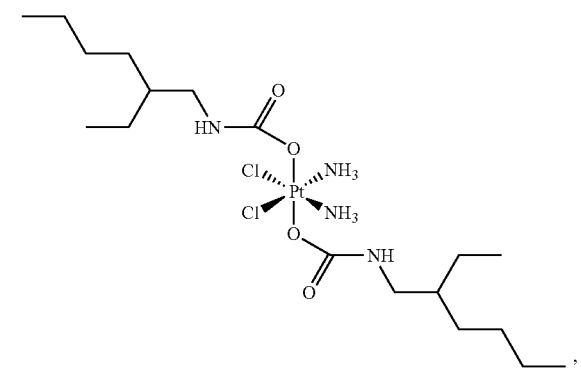
31
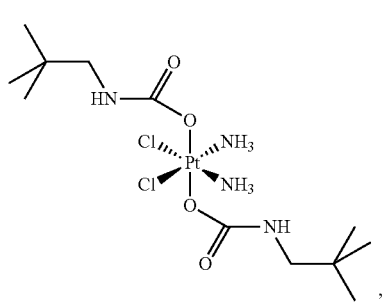

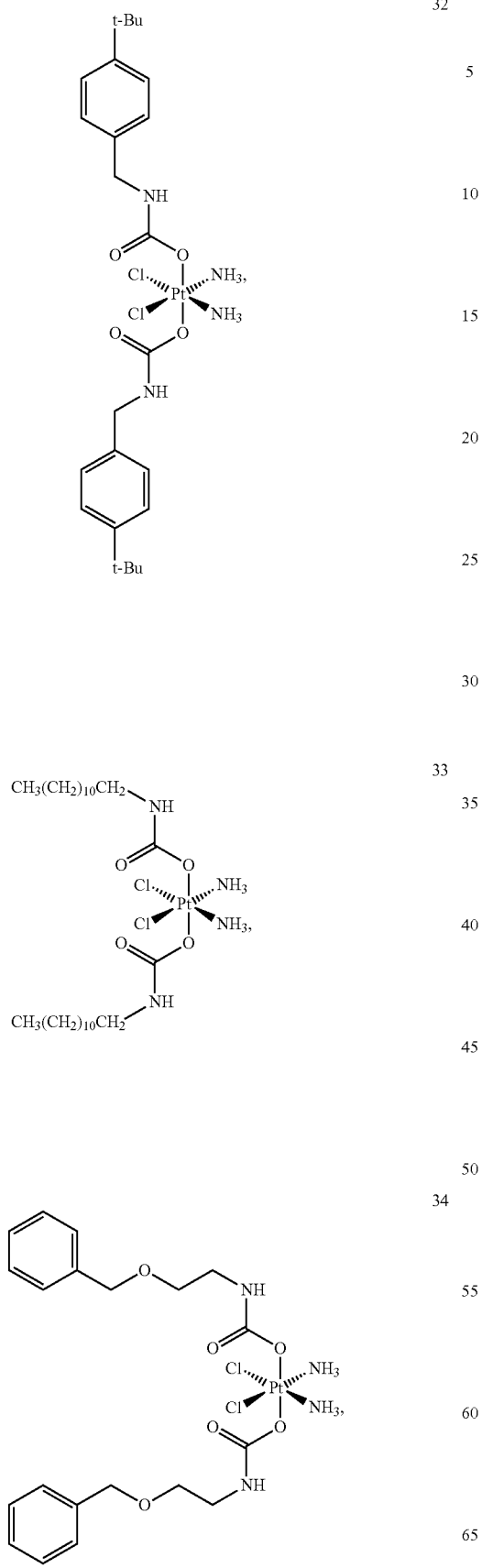
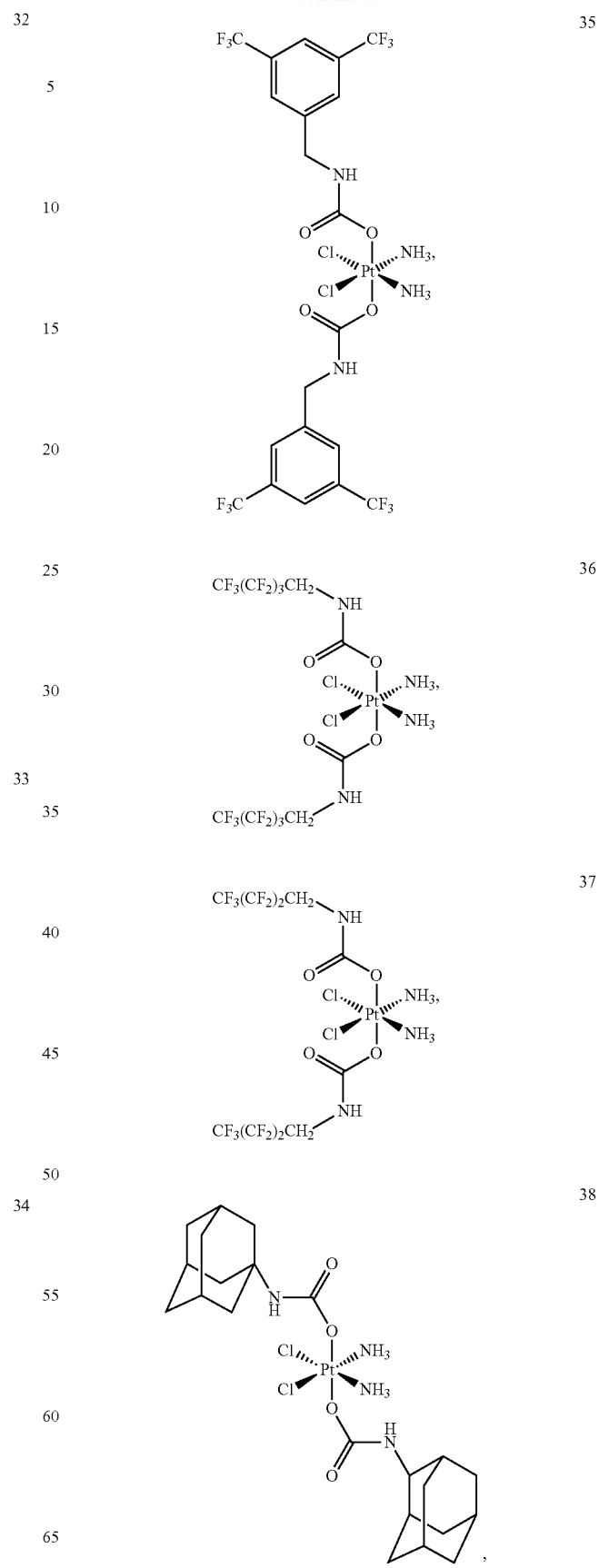

39

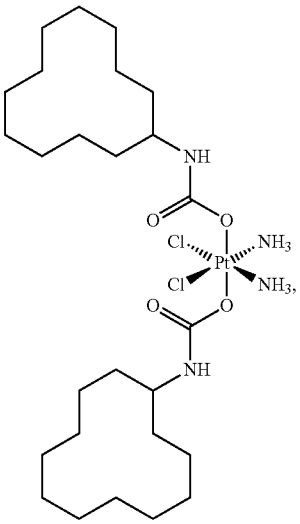

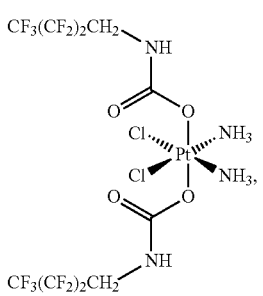

40

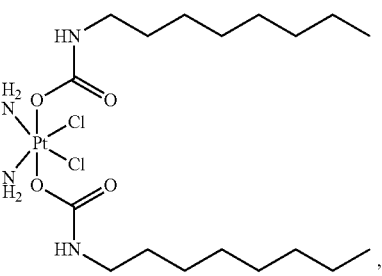

41

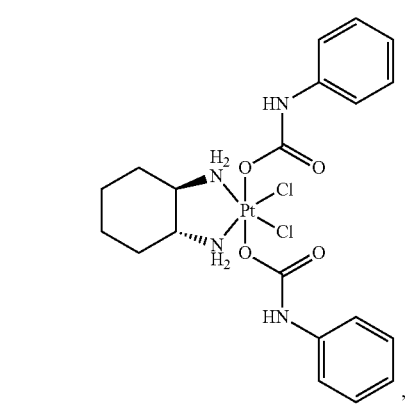

42

43

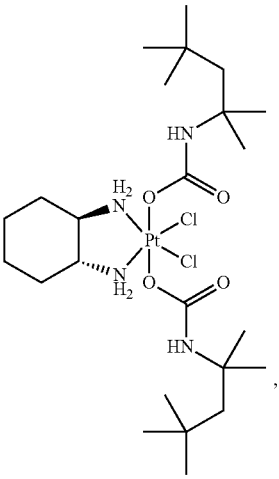

44

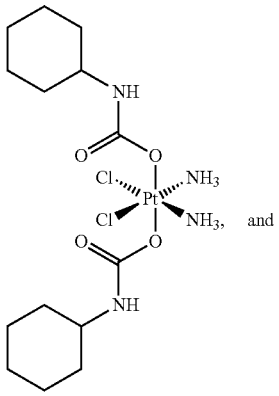

and

45

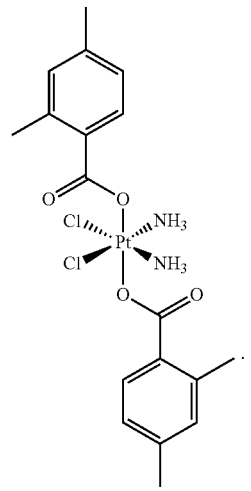

As described herein, some compounds of the present teachings may be provided as a salt comprising a charged platinum complex and a counter ion, including a pharmaceutically acceptable counter ion. The counter ion may be a weak or non-nucleophilic stabilizing ion, having a charge of (−1), (−2), (−3), (+1), (+2), (+3), etc. In some embodiments, the counter ion has a charge of (−1). In other embodiments, the counter ion has a charge of (−2). In some embodiments, the counter ion has a charge of (+1). In other embodiments, the counter ion has a charge of (+2).

The present teachings further comprise compositions (including pharmaceutical compositions) each comprising one or more of the compounds as described herein. In various embodiments, a composition of the present teachings comprises a particle and a compound described herein. In some embodiments, the particle comprises a base component forming an exterior part and an interior part. In certain embodiments, the interior of the particle is more hydrophobic than the exterior of the particle. In certain other embodiments, the interior is more hydrophilic than the exterior.

In various embodiments, the base component comprises a polymer, a small molecule, or a mixture thereof. The base component can be biologically derived. For example, the small molecule can be, for example, a lipid. A "lipid," as used herein, refers to a hydrophobic or amphiphilic small molecule. Without attempting to limit the scope of the present teachings, lipids, because of their amphiphilicity, can form particles, including liposomes and micelles.

In some embodiments, the base component comprises a polymer. For example, the polymer can be a biopolymer. Non-limiting examples include peptides or proteins (i.e., polymers of various amino acids), nucleic acids such as DNA or RNA. In certain embodiments, the polymer is amphiphilic, i.e., having a hydrophilic portion and a hydrophobic portion, or a relatively hydrophilic portion and a relatively hydrophobic portion.

In various embodiments, the base component is biocompatible, i.e., it does not typically induce an adverse response when inserted or injected into a subject, for example, at least in the amount that would be included in a therapeutically effective amount of a composition of the present teachings. The adverse response can include significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system (e.g., in a majority of subjects), i.e., a non-biocompatible material implanted into a subject provokes an immune response in the subject that is severe enough such that the rejection of the material by the immune system cannot be adequately controlled, and often is of a degree such that the material must be removed from the subject.

Non-limiting examples of biocompatible polymers that may be useful in various embodiments of the present invention include polyester (e.g., aliphatic polyester). In various embodiments, the polymers include polydioxanone (PDO), polyhydroxyalkanoate, polyhydroxybutyrate, poly(glycerol sebacate), polyglycolide, polylactide, polycaprolactone, poly(butylene succinate), polycarbonate, or copolymers or derivatives including these and/or other polymers.

In various embodiments, the base component is biodegradable, i.e., the polymer can be degraded, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

Examples of biodegradable polymers include polyester. In various embodiment, the biodegradable polymer includes, but are not limited to, poly(lactide) (or poly(lactic acid)), poly(glycolide) (or poly(glycolic acid)), poly(orthoesters), poly(caprolactones), polylysine, poly(ethylene imine), poly (acrylic acid), poly(urethanes), poly(anhydrides), poly(esters), polycarbonates (including poly(trimethylene carbonate)), poly(ethyleneimine), poly(acrylic acid), poly (urethane), poly(beta amino esters) or the like, and copolymers or derivatives of these and/or other polymers, for example, poly(lactide-co-glycolide) (PLGA).

In various embodiments, the base component comprises polylactide or poly(lactic acid). In various embodiments, the base component comprises poly(glycolide). In various embodiments, the base component comprises poly(lactide-co-glycolide). A person with ordinary skill in the art can choose polylactide, polyglycolide, or poly(lactide-co-glycolide) of different molecular weights according to various applications. In some embodiments, the polylactide, polyglycolide, or poly(lactide-co-glycolide) has a number average molecular weight of about 5 kDa to about 250 kDa. For example, the polylactide, polyglycolide, or poly(lactide-co-glycolide) has a number average molecular weight of about 15 kDa to about 200 kDa. In certain embodiments, the polylactide, polyglycolide, or poly(lactide-co-glycolide) has a number average molecular weight of about 5 kDa to about 10 kDa, about 10 kDa to about 20 kDa, about 20 kDa to about 30 kDa, about 30 kDa to about 40 kDa, about 40 kDa to about 50 kDa, about 50 kDa to about 60 kDa, about 60 kDa to about 70 kDa, about 70 kDa to about 80 kDa, about 80 kDa to about 90 kDa, about 90 kDa to about 100 kDa, about 100 kDa to about 110 kDa, about 110 kDa to about 120 kDa, about 120 kDa to about 130 kDa, about 130 kDa to about 140 kDa, about 140 kDa to about 150 kDa, about 150 kDa to about 160 kDa, about 160 kDa to about 170 kDa, about 170 kDa to about 180 kDa, about 180 kDa to about 190 kDa, or about 190 kDa to about 200 kDa. In certain embodiments, the polylactide, polyglycolide, or poly(lactide-co-glycolide) has a number average molecular weight of about 10 kDa to about 250 kDa, about 15 kDa to about 200 kDa, about 20 kDa to about 150 kDa, about 30 kDa to about 100 kDa, or about 40 kDa to about 80 kDa. For example, the polylactide, polyglycolide, or poly(lactide-co-glycolide) can have a number average molecular weight of about 15 kDa, about 25 kDa, about 35 kDa, about 50 kDa, about 60 kDa, about 70 kDa, about 80 kDa, about 90 kDa, about 100 kDa, or about 110 kDa. In particular embodiments, the polylactide, polyglycolide, or poly(lactide-co-glycolide) has a number average molecular weight of about 15 kDa. In particular embodiments, the polylactide, polyglycolide, or poly(lactide-co-glycolide) has a number average molecular weight of about 25 kDa, about 105 kDa, or about 108 kDa. In some embodiments, the number average molecular weight is selected from those described above.

In various embodiments, the base component comprises at least some other repeating units. Nonexclusive examples of such other repeating units include a poly(alkylene glycol) (also known as poly(alkylene oxide)), such as poly(propylene glycol), or poly(ethylene oxide), also known as poly (ethylene glycol) ("PEG"), having the formula —(CH$_2$—CH$_2$—O)$_n$—, where n is any positive integer. The poly (ethylene glycol) units may be present within the polymeric base component in any suitable form. For instance, the polymeric base component may be a block copolymer where one of the blocks is poly(ethylene glycol). A polymer having poly(ethylene glycol) repeating units is also referred to as a "PEGylated" polymer. Such polymers can sometimes control inflammation and/or immunogenicity (i.e., the ability to provoke an immune response), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. For example, PEGylation may be used to create particles which comprise an interior that is more hydrophobic than the exterior of the particles. In some cases, the addition of poly(ethylene glycol) repeating units may increase plasma half-life of the polymeric conjugate, for instance, by decreasing the uptake of the polymer by the phagocytic system while decreasing transfection/uptake efficiency by cells.

In various embodiments, the PEG unit has a number average molecular weight of about 1 kDa to about 25 kDa. For example, the PEG unit can have a number average molecular weight of about 1 kDa to about 2 kDa, about 2 kDa to about 3 kDa, about 3 kDa to about 4 kDa, about 4 kDa to about 5 kDa, about 5 kDa to about 6 kDa, about 6 kDa to about 7 kDa, about 7 kDa to about 8 kDa, about 8 kDa to about 9 kDa, about 9 kDa to about 10 kDa, about 10 kDa to about 12 kDa, about 12 kDa to about 14 kDa, about 14 kDa to about 16 kDa, about 16 kDa to about 18 kDa, about 18 kDa to about 20 kDa, about 20 kDa to about 22 kDa, about 22 kDa to about 24 kDa, or, about 24 kDa to about 25 kDa. In some embodiments, the PEG unit has a number average molecular weight of about 1 kDa to about 10 kDa. In certain embodiments, the PEG unit has a number average molecular weight of about 2 kDa to about 8 kDa, or about 3 kDa to about 7 kDa, or about 4 kDa to about 6 kDa. For example, the PEG unit has a number average molecular weight of about 2 kDa to about 6 kDa or about 3 kDa to about 5 kDa. In particular embodiments, the PEG unit has a number average molecular weight of about 3 KDa, 4 kDa, 5 kDa, or 6 kDa.

In various embodiments, the base component comprises a polylactide, a polyglycolide, or poly(lactide-co-glycolide) and a PEGylated polylactide, a PEGylated polyglycolide, or a PEGylated poly(lactide-co-glycolide). The weight percentage of the PEGylated polymer in the base component can be from 0% to 100%, including about 5% to about 95%, about 10% to about 90%, about 20% to about 80%, about 30% to about 70%, or about 40% to about 60%. In some embodiments, the weight percentage of the PEGylated polymer in the base component is about 30% to about 95% or about 40% to about 90%. In particular embodiments, the weight percentage of the PEGylated polymer in the base component is about 40%, 50%, 60%, 70%, 80%, 90%, or 100%. For example, the weight percentage of the PEGylated polymer in the base component is about 50%, about 60%, or about 85%. In some embodiments, the weight percentage of the PEGylated polymer in the base component is a percentage disclosed above, e.g., the weight percentage is 5% to 95%, etc.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, for example, by ring opening polymerization techniques, or the like. In addition, certain embodiments of the invention are directed towards copolymers containing poly(ester-ether)s, e.g., polymers having repeating units joined by ester bonds (e.g., R—C(O)—O—R' bonds) and ether bonds (e.g., R—O—R' bonds).

In various embodiments, the particle comprises one or more compounds of the present teachings. In some embodiments, at least one of the compounds is contained within a particle of the present teachings. The term "contained within" may mean "located in a cavity of," "entirely embedded in," or "partially embedded in." For example, at least one of the compounds can be located in a cavity formed in a particle of the present teachings or otherwise embedded in a particle of the present teachings. In certain embodiments, at least one of the compounds is located in the cavity of a particle. In certain embodiments, at least one of the compounds is entirely embedded in a particle. In certain embodiments, at least one of the compounds is partially embedded in a particle.

In various embodiments, a substantial amount of at least one of the compounds is contained within particles of the present teachings. The percentage of a compound included in the particles that is contained within the particles can sometimes be used to measure the efficiency of the compound being encapsulated in the particle (i.e., the "encapsulation efficiency"). In some embodiments, about 90% or greater, about 80% or greater, about 70% or greater, or about 60% or greater of the total amount of at least one of the compounds included in the particles is contained within the particles. In certain embodiments, about 80% or greater of the total amount of at least one of the compounds included in the particles is contained within the particles. In certain embodiments, about 90% or greater of the total amount of at least one of the compounds included in the particles is contained within the particles. In certain embodiments, about 95% or greater of the total amount of at least one of the compounds included in the particles is contained within the particles.

In various embodiments, about 50% and greater, about 40% or greater, about 30% or greater, about 20% or greater, or about 10% or greater of the total amount of at least one of the compounds included in particles of the present teachings is contained within the particles. In some embodiments, about 10% or greater of the total amount of at least one of the compounds included in the particles is contained within the particles. In some embodiments, about 20% or greater of the total amount of at least one of the compounds included in the particles is contained within the particles. In some embodiments, about 30% or greater of the total amount of at least one of the compounds included in the particles is contained within the particles. In some embodiments, about 40% or greater of the total amount of at least one of the compounds included in the particles is contained within the particles. In some embodiments, about 50% or greater of the total amount of at least one of the compounds included in the particles is contained within the particles.

In some embodiments, the total percentage (for example, the total weight percentage) of the compound in the particles (sometimes called the "percentage loading") is greater than about 0.01%, greater than about 0.05%, greater than about 0.1%, greater than about 0.5%, greater than about 1%, greater than about 2%, greater than about 5%, greater than about 10%, greater than about 15%, greater than about 20%, greater than about 25%, greater than about 30%, greater than about 35%, greater than about 40%, greater than about 45%, greater than about 50%, greater than about 55%, or greater. In some embodiments, the percent loading is between about 0.01% and about 50%, between about 0.05% and about 30%, between about 0.1% and about 10%, between about 1% and about 10%, between about 0.05% and about 30%, between about 0.05% and about 10%, between about 0.1% and about 50%, or any range therein. In certain embodiments, the percentage loading is about 2%, about 3%, about 4%, about 5%, about 6%, about 7%, or about 8%. In particular embodiments, the percentage loading is about 5%, about 6%, about 7%, about 8%, about 9%, or about 10%.

In various embodiments, the ratio of a compound of the present teachings to a base component of the present teachings in a solution prior to formation of particles may affect the encapsulation efficiency, the percent loading of the compound in the particle, and/or the mean size of the particle. For example, an increase in the percent weight of the compound to the percent weight of the base component may increase the encapsulation efficiency or the percent loading of the compound within the particle. However, the encapsulation efficiency or the percent loading of the compound in the particles formed may or may not be related to the weight percent of the compound provided during formation of the particles.

In some embodiments, the percent weight of the compound provided in a mixture comprising the compound and the base component is at least about 5%, at least about 10%, at least about 20%, at least about 30%, at least about 40%, at least about 50%, at least about 60%, at least about 70%, at least about 80%, at least about 90%, at least about 100%, or greater. In certain embodiments, the percent weight is between about 5% and about 90%, between about 10% and about 80%, between about 10% and about 50%, between about 50% and about 90%, or any range therein. In particular embodiments, the weight percentage is about 5% to about 30% or about 5% to about 20%. For example, the weight percentage can be about 10%.

Without wishing to be bound by theory, the lipophilicity of a compound in some instances can change the encapsulation efficiency or/and the percentage loading of a compound in particles of the present teachings. In some embodiments, a compound with a relatively great lipophilicity can, sometimes surprisingly, increase the encapsulation efficiency. In some embodiments, a compound with a relatively great lipophilicity can, sometimes surprisingly, increase the percentage loading of the compound in the particles. The lipophilicity of a compound can sometimes be reflected by the solubility of the compound in an organic solvent. For example, ethyl acetate can be used to estimate the lipophilicity of a compound.

In various embodiments, compounds of the present teachings have a good solubility in ethyl acetate. For example, the compound can have a ethyl acetate solubility in the amount of greater than about 10 mg/ML, greater than about 50 mg/mL, greater than about 100 mg/mL, greater than about 150 mg/mL, greater than about 200 mg/mL, greater than about 300 mg/mL, greater than about 500 mg/mL, or greater than about 1,000 mg/mL. In some embodiments, the compound has a solubility between about 10 mg/mL and about 200 mg/mL. In certain embodiments, the compound has a solubility of about 10 mg/mL, about 50 mg/mL, about 100 mg/mL, about 150 mg/mL, or about 200 mg/mL. The solubility in ethyl acetate can be used as a surrogate for solvation by PLA and PLGA polymers. In various embodiments, compounds of the present teachings have a good lipophilicity. In various embodiments, compounds of the present teachings have good encapsulation efficiency, sometimes leading to a good drug loading. Without limiting the scope of the present teachings, a great solubility in ethyl acetate sometimes correlates to a good lipophilicity; and a great lipophilicity sometimes correlates to a good encapsulation efficiency, e.g., at least 10%, at least 25%, at least 40%, at least 50%, at least 60%, or at least 70% encapsulation efficiency. For example, compounds 45, 29, and 43 in Table 4 each shows an increased solubility in ethyl acetate, an increased encapsulation efficiency, and an increased maximum drug loading.

Without wishing to be bound by theory, the size of a particle may alter the delivery (e.g., loss of payload, drug efflux, aggregation, delivery to desired location, etc.) of a compound of the present teachings from the particles. The size of the particles used in a delivery system may be selected based on the application, and will be readily known to those of ordinary skill in the art. For example, particles of smaller size (e.g., <200 nm) may be selected if systematic delivery of the particles throughout a patient's bloodstream is desired. As another example, particles of larger size (e.g., >200 nm) may be selected if sequestering of the particles by a patient's reticuloendothelial system upon injection is desired (e.g., sequestering of the particles in the liver, spleen, etc.). The desired length of time of delivery may also be considered when selecting particle size. For example, smaller particles may circulate in the blood stream for longer periods of time than larger particles.

In some embodiments, the particles may substantially accumulate at the site of a tumor. Without attempting to limit the scope of the present teaching, the accumulation may be due, at least in part, to the presence of a targeting moiety associated with the particle, as described herein; or, at least in part, due to an enhanced permeability and retention (EPR) effect, which allows for particles to accumulate specifically at a tumor site. The EPR effect will be known to those of ordinary skill in the art and refers to the property by which certain sizes of material (e.g., particles) tend to accumulate in tumor tissue much more than they do in normal tissues.

In various embodiments, a particle may be a nanoparticle, i.e., the particle has a characteristic dimension of less than about 1 micrometer, where the characteristic dimension of a particle is the diameter of a perfect sphere having the same volume as the particle. The plurality of particles can be characterized by an average diameter (e.g., the average diameter for the plurality of particles). In some embodiments, the diameter of the particles may have a Gaussian-type distribution. In some embodiments, the plurality of particles have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm. In some embodiments, the particles have an average diameter of at least about 5 nm, at least about 10 nm, at least about 30 nm, at least about 50 nm, at least about 100 nm, at least about 150 nm, or greater. In certain embodiments, the plurality of the particles have an average diameter of about 10 nm, about 25 nm, about 50 nm, about 100 nm, about 150 nm, about 200 nm, about 250 nm, about 300 nm, about 500 nm, or the like. In some embodiments, the plurality of particles have an average diameter between about 10 nm and about 500 nm, between about 50 nm and about 400 nm, between about 100 nm and about 300 nm, between about 150 nm and about 250 nm, between about 175 nm and about 225 nm, or the like. In some embodiments, the plurality of particles have an average diameter between about 10 nm and about 500 nm, between about 20 nm and about 400 nm, between about 30 nm and about 300 nm, between about 40 nm and about 200 nm, between about 50 nm and about 175 nm, between about 60 nm and about 150 nm, between about 70 nm and about 130 nm, or the like. For example, the average diameter can be between about 70 nm and 130 nm. In some embodiments, the plurality of particles have an average diameter between about 20 nm and about 220 nm, between about 30 nm and about 200 nm, between about 40 nm and about 180 nm, between about 50 nm and about 170 nm, between about 60 nm and about 150 nm, between about 70 nm and about 130 nm, or the like.

Another aspect of the present teachings relates to systems and methods of making the disclosed particles, including nanoparticles.

In various embodiments, a method of making the particles comprises providing a compound disclosed herein; providing a base component (e.g., PLA-PEG or PLGA-PEG); combining the compound and the base component in an organic solution to form a first organic phase; and combining the first organic phase with a first aqueous solution to form a second phase; emulsifying the second phase to form an emulsion phase; and recovering particles. In various embodiments, the emulsion phase is further homogenized.

In some embodiments, the first phase includes about 5 to about 50% weight, e.g. about 1 to about 40% solids, or about 5 to about 30% solids, e.g. about 5%, 10%, 15%, and 20%, of the compound and the base component. In certain embodiments, the first phase includes about 5% weight of the compound and the base component. In various embodiments, the organic phase comprises acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or a combination thereof. In some embodiments, the organic phase includes benzyl alcohol, ethyl acetate, or a combination thereof.

In various embodiments, the aqueous solution comprises water, sodium cholate, ethyl acetate, or benzyl alcohol. In various embodiments, a surfactant is added into the first phase, the second phase, or both. A surfactant, in some instances, can act as an emulsifier or a stabilizer for a composition disclosed herein. A suitable surfactant can be a cationic surfactant, an anionic surfactant, or a nonionic surfactant. In some embodiments, a surfactant suitable for making a composition described herein includes sorbitan fatty acid esters, polyoxyethylene sorbitan fatty acid esters, or polyoxyethylene stearates. Examples of such fatty acid ester nonionic surfactants are the Span™ Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates. In certain embodiments, the aqueous solution also comprises a surfactant (e.g., an emulsifier), including a polysorbate. For example, the aqueous solution can include polysorbate 80. In some embodiments, a suitable surfactant includes a lipid-based surfactant. For example, the composition can include 1,2-dihexanoyl-sn-glycero-3-phosphocholine, 1,2-diheptanoyl-sn-glycero-3-phosphocholine, PEGylated 1,2-distearoyl-sn-glycero-3-phosphoethanolamine (including PEG5000-DSPE), PEGylated 1,2-dioleoyl-sn-glycero-3-phosphoethanolamine (including 1,2-dioleoyl-sn-glycero-3-phosphoethanolamine-N-[methoxy(polyethylene glycol)-5000] (ammonium salt)).

Emulsifying the second phase to form an emulsion phase may be performed in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g. a probe sonicator or a high pressure homogenizer, e.g. by using 1, 2, 3, or more passes through a homogenizer. For example, when a high pressure homogenizer is used, the pressure used may be about 4,000 to about 12,000 psi, or about 5,000 to about 10,000 psi, e.g. 5,000 or 10,000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. Quenching may be performed at least partially at a temperature of about 5° C. or less. For example, water used in the quenching may be at a temperature that is less that room temperature (e.g. about 0 to about 10° C., or about 0 to about 5° C.).

In various embodiments, the particles are recovered by filtration. For example, ultrafiltration membranes can be used. Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (5-25 nm) may be used.

In various embodiments, the particles are freeze-dried or lyophilized, in some instances, to extend their shelf life. In some embodiments, the composition also includes a lyoprotectant. In certain embodiments, a lyoprotectant is selected from a sugar, a polyalcohol, or a derivative thereof. In particular embodiments, a lyoprotectant is selected from a monosaccharide, a disaccharide, a cyclic oligosaccharide, a polysaccharide, or a mixture thereof. For example, a lyoprotectant can be sucrose, lactulose, trehalose, lactose, glucose, maltose, mannitol, cellobiose, cyclodextrin, or a mixture thereof.

In various embodiments, a compound of the present teachings contained within a particle is released in a controlled manner. The release can be in vitro or in vivo. For example, particles of the present teachings can be subject to a release test under certain conditions, including those specified in the U.S. Pharmacopeia and variations thereof.

In various embodiments, less than about 90%, less than about 80%, less than about 70%, less than about 60%, less than about 50%, less than about 40%, less than about 30%, less than about 20% of the compound of the present teachings contained within particles is released in the first hour after the particles are exposed to the conditions of a release test. In some embodiments, less that about 90%, less than about 80%, less than about 70%, less than about 60%, less than about 50% of the compound of the present teachings contained within particles is released in the first hour after the particles are exposed to the conditions of a release test. In certain embodiments, less than about 50% of the compound contained within particles is released in the first hour after the particles are exposed to the conditions of a release test.

With respect to a compound of the present teachings being released in vivo, for instance, the compound contained within a particle administered to a subject may be protected from a subject's body, and the body may also be isolated from the compound until the compound is released from the particle.

Thus, in some embodiments, the compound may be substantially contained within the particle until the particle is delivered into the body of a subject. For example, less than about 90%, less than about 80%, less than about 70%, less than about 60%, less than about 50%, less than about 40%, less than about 30%, less than about 20%, less than about 15%, less than about 10%, less than about 5%, or less than about 1% of the total compound is released from the particle prior to the particle being delivered into the body, for example, a treatment site, of a subject. In some embodiments, the compound may be released over an extended period of time or by bursts (e.g., amounts of the compound are released in a short period of time, followed by a periods of time where substantially no compound is released). For example, the compound can be released over 6 hours, 12 hours, 24 hours, or 48 hours. In certain embodiments, the compound is released over 1 week or 1 month.

These and other embodiments of the present teachings may also involve promotion of the treatment of cancer or tumor according to any of the techniques and compositions and combinations of compositions described herein.

In various embodiments, methods for treating a subject having a cancer are provided, wherein the method comprises administering a therapeutically-effective amount of a compound, as described herein, to a subject having a cancer, suspected of having cancer, or having a predisposition to a cancer. In some embodiments, the subject may be otherwise free of indications for treatment with said compound. In some embodiments, methods include use of cancer cells, including but not limited to mammalian cancer cells. In some instances, the mammalian cancer cells are human cancer cells.

In some embodiments, the compounds of the present teachings have been found to inhibit cancer growth, including proliferation, invasiveness, and metastasis, thereby rendering them particularly desirable for the treatment of cancer.

In some embodiments, the compounds of the present teachings may be used to prevent the growth of a tumor or cancer, and/or to prevent the metastasis of a tumor or cancer. In some embodiments, compositions of the present teachings may be used to shrink or destroy a cancer.

In some embodiments, a compound provided herein is useful for inhibiting proliferation of a cancer cell. In some embodiments a compound provided herein is useful for inducing cell death of a cancer cell or both inhibiting proliferation or inducing cell death of a cancer cell.

The cancers treatable by methods of the present teachings generally occur in mammals. Mammals include, for example, humans and non-human primates, as well as pet or companion animals, such as dogs and cats, laboratory animals, such as rats, mice and rabbits, and farm animals, such as horses, pigs, sheep, and cattle. In various embodiments, the cancer is lung cancer, breast cancer, colorectal cancer, ovarian cancer, bladder cancer, prostate cancer, cervical cancer, renal cancer, leukemia, central nervous system cancers, myeloma, and melanoma. In some embodiments, the cancer is lung cancer. In certain embodiments, the cancer is human lung carcinoma and/or normal lung fibroblast.

The following examples are intended to illustrate certain embodiments of the present teachings, but do not necessarily exemplify the full scope of the present teachings and therefore should not be construed to limit the scope of the present teachings.

EXAMPLES

Example 1(a)

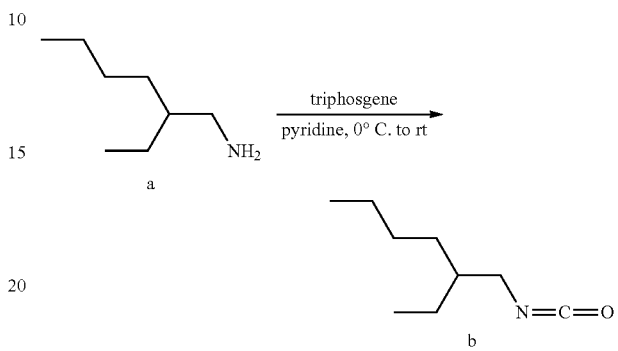

To a solution of triphosgene (1.8 g, 6 mmol) in anhydrous tetrahydrofuran (THF, 20 mL) cooled to 0° C. was added N,N-diisopropylethylamine (DIPEA, 3.6 mL, 24 mmol) followed by a (1.6 g, 12 mmol) as a solution in anhydrous THF (20 mL) and the reaction was warmed to room temperature and stirred for 3.5 hours (h). The reaction was concentrated in vacuo to afford the crude product b, which was used in the next step without further purification.

Example 1(b)

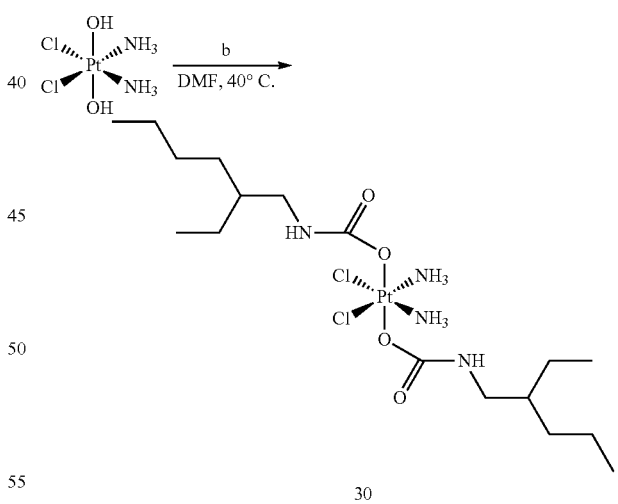

To a suspension of cis,cis,trans-[Pt(NH$_3$)$_2$Cl$_2$(OH)$_2$] (0.20 g, 0.60 mmol) in 1 mL of dimethylformamide (DMF) was added a 1 mL DMF solution of 4 mol equivalent of the isocyanate b (crude product from the above step). The resulting mixture was stirred for 12 h at 40° C. Excess ethyl acetate was added, and the solution was filtered to remove the unreacted di-hydroxyplatinum. The filtrate was washed several times with H$_2$O and concentrated.

The white solid was precipitated with the addition of hexane, and washed thoroughly with hexane. The solid was dissolved in methanol (MeOH) and H$_2$O was added to the stirred solution. The precipitated desired product 30 was collected by filtration and dried under vacuum. White solid (80 mg, 20% yield). $^1$H NMR (500 MHz, DMSO): δ 6.68 (s, 6H), 6.47 (s, 2H), 2.82 (s, 4H), 1.31-1.15 (m, 18H), 0.86 (t, J=9.0 Hz, 6H), 0.80 (t, J=9.0 Hz, 6H). LC-MS m/z: 645 (M+H$^+$).

Example 2(a)

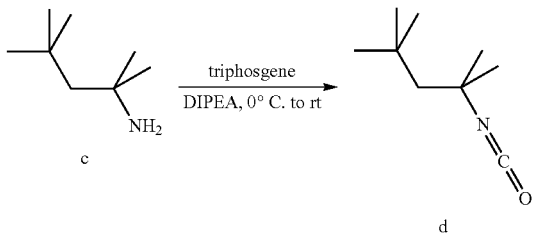

To a solution of triphosgene (1.8 g, 6 mmol) in anhydrous THF (20 mL) cooled to 0° C. was added DIPEA (4.2 mL, 24 mmol) followed by c (1.6 g, 12 mmol) as a solution in anhydrous THF (20 mL) and the reaction was warmed to room temperature and stirred for 3.5 h. The reaction was concentrated in vacuo. The residue was dissolved in dichloromethane and washed with an equal volume of 0.1 N HCl. The organic layer was dried (Na$_2$SO$_4$) and concentrated in vacuo to afford the product d as a brown oil (743 mg, 87% yield) which was used in the next step without further purification.

Example 2(b)

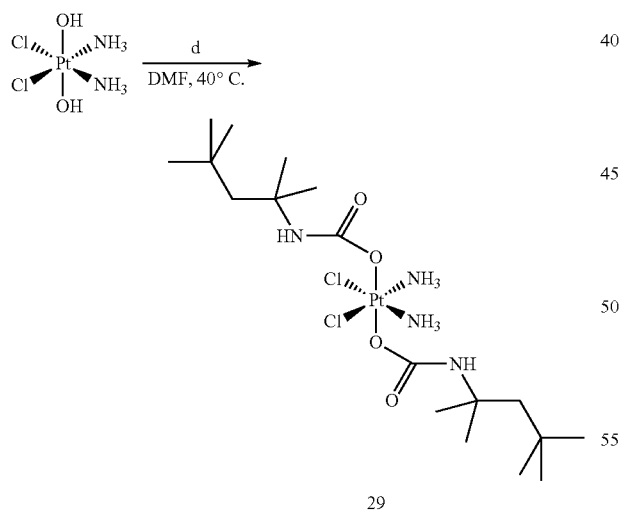

To a suspension of cis,cis,trans-[Pt(NH$_3$)$_2$Cl$_2$(OH)$_2$] (0.20 g, 0.60 mmol) in 1 mL of DMF was added a 1 mL DMF solution of 4 mol equivalent of the isocyanate d (crude product from the above step). The resulting mixture was stirred for 12 h at 40° C. Excess ethyl acetate was added and the solution was filtered to remove the unreacted di-hydroxyplatinum. The filtrate was washed several times with H$_2$O and concentrated. The white solid was precipitated with the addition of hexane and washed thoroughly with hexane. The solid was dissolved in MeOH and H$_2$O was added to the stirred solution. The precipitated desired product 29 was collected by filtration and dried under vacuum. White solid (80 mg, 20% yield). $^1$H NMR (500 MHz, DMSO): δ 6.62 (s, 6H), 6.00 (s, 2H), 1.61 (s, 4H), 1.21 (s, 12H), 0.94 (s, 18H). LC-MS m/z: 645 (M$^+$).

Example 3(a)

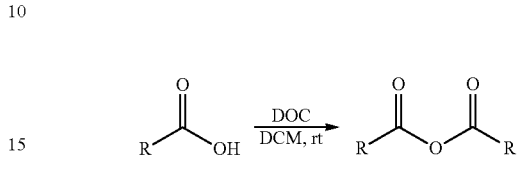

A stirred solution of carboxylic acid (1 eq.) in dichloromethane was added N,N'-dicyclohexylcarbodiimide (DCC, 0.5 eq.) in portions at room temperature and then stirred for a several hours. The white solid was removed by filtration and the filtrate was concentrated to give the crude product without further purifications.

| Anhydride | RCO$_2$H = |
|---|---|
| e | 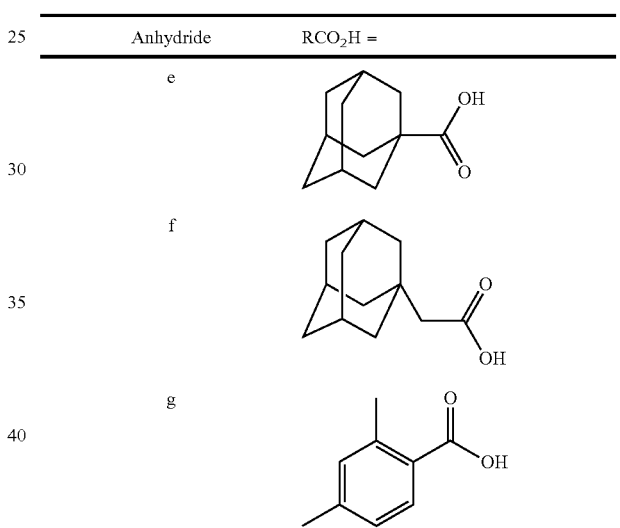 |
| f | |
| g | |

Example 3(b)

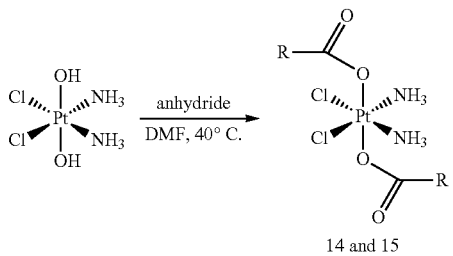

To a suspension of cis,cis,trans-[Pt(NH$_3$)$_2$Cl$_2$(OH)$_2$] (0.20 g, 0.60 mmol) in 1 mL of DMF was added a 1 mL DMF solution containing 4 mol equivalent of anhydride e, f, or g (crude product from the above step). The resulting mixture was stirred for 12 h at 40° C. Ethyl acetate was added. The precipitate was collected by filtration and then dissolved in MeOH, which was then added dropwise to the well-stirred H₂O. The precipitated desired product 14, 15, or 45 was collected by filtration and dried under vacuum.

| Compound | R = |
|---|---|
| 14 | (1-adamantyl) |
| 15 | (1-adamantylmethyl) |
| 45 | (2,4-dimethylphenyl) |

14: ¹H NMR (500 MHz, DMSO): δ 6.45 (s, 6H), 1.91 (s, 6H), 1.77 (s, 12H), 1.66-1.60 (s, 12H). LC-MS m/z: 659 (M+H⁺).

15: ¹H NMR (500 MHz, DMSO): δ 6.52 (s, 6H), 1.92-1.89 (m, 10H), 1.65-1.59 (s, 24H). LC-MS m/z: 687 (M+H⁺).

45: ¹H NMR (500 MHz, DMSO): δ 7.7 (d, 2H), 7.0 (s and d, 4H), 6.7 (s, 6H), 2.5 (s, 6H), 2.3 (s, 6H). LC-MS m/z: 600 (M+H⁺).

Example 4(a)

A solution of carboxylic acid (1 eq.) and diphenylphosphoryl azide (DPPA, 1.2 eq.) in dry toluene was added triethylamine (TEA, 1.5 eq.) and then stirred at 50° C. for 2 h. The mixture was cooled to room temperature and washed several times with H₂O. The organic phase was dried over Na₂SO₄ and filtered. The filtrate was heated under reflux overnight and concentrated to give the crude products h-k, which were used in the next step without further purifications.

| isocyanate | R = |
|---|---|
| h | (cyclohexyl) |
| i | (diphenylmethyl) |
| j | (1-adamantyl) |
| k | (n-octyl) |

Example 4(b)

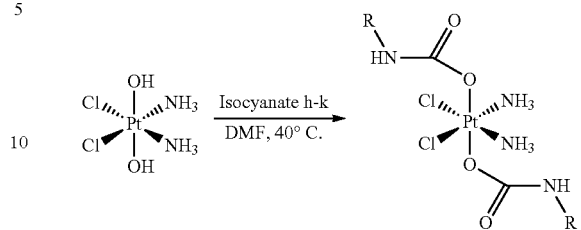

To a suspension of cis,cis,trans-[Pt(NH₃)₂Cl₂(OH)₂] (0.20 g, 0.60 mmol) in 1 mL of DMF was added a 1 mL DMF solution containing 4 mol equivalent of one of h-k (crude product from the above step). The resulting mixture was stirred for 12 h at 40° C. DMF was removed by concentration and the residue was dissolved in MeOH, which was added dropwise to a well-stirred solution of diethylether. The white solid was precipitate and collected by filtration to give the desired product.

| Compound | R = |
|---|---|
| 44 | (cyclohexyl) |
| 27 | (diphenylmethyl) |
| 38 | (1-adamantylmethyl) |
| 28 | (n-octyl) |

44: ¹H NMR (500 MHz, DMSO): δ 6.67 (s, 6H), 6.42 (s, 2H), 3.19 (s, 2H), 1.71-1.50 (m, 10H), 1.23-1.03 (m, 10H). LC-MS m/z: 581 (M+H⁺).

27: ¹H NMR (500 MHz, DMSO): δ 7.71 (d, J=9.5 Hz, 2H), 7.35 (d, J=7.5 Hz, 8H), 7.27 (t, J=7.5 Hz, 8H), 7.18 (t, J=7.5 Hz, 4H), 6.69 (s, 6H), 5.84 (d, J=9.5 Hz, 2H). LC-MS m/z: 753 (M+H⁺).

38: ¹H NMR (500 MHz, DMSO): δ 6.64 (s, 6H), 5.96 (s, 2H), 1.96 (s, 6H), 1.84 (s, 12H), 1.57 (s, 12H). LC-MS m/z: 689 (M+H⁺).

28: ¹H NMR (500 MHz, DMSO): δ 6.67 (s, 6H), 6.51 (s, 2H), 2.88 (d, J=6.0 Hz, 4H), 1.34-1.23 (m, 24H), 0.86 (t, J=6.5 Hz, 6H). LC-MS m/z: 645 (M+H⁺).

Example 5

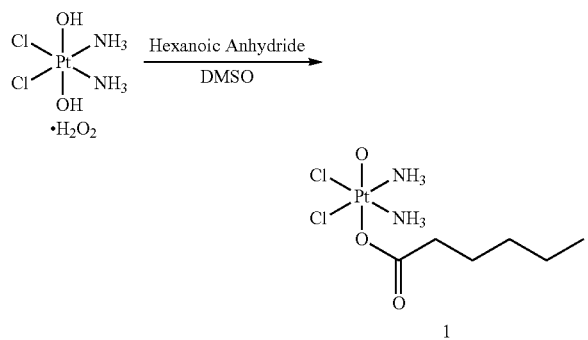

Dihydroxy-cisplatin(IV)-monoperoxide (1.0 g, 2.7 mmol) was added to a 250 mL round bottom flask with a stir bar. DMSO (80 mL) was added and the resulting mixture was stirred at RT. Hexanoic anhydride (623 µL, 2.7 mmol) was added to the reaction mixture in equal portions over the course of 2 days (i.e., at t=0, 8 h, 24 h, and 36 h). The reaction mixture was stirred at room temperature for an additional 16 h, at which point the DMSO was removed by lyophilization. An off-white powder was obtained as compound 1 in 90% yield (1.05 g). The product was analyzed by HPLC-MS. The peak at 2.76 minutes affords the product parent ion of 433 Da (M+H) (Water ZQ Micromass), which corresponds to compound 1. $^1$H NMR (Varian 400 MHz) CDCl$_3$: δ 2.27-2.26 (m, 1H), 2.12 (t, J=7 Hz, 1H), 1.40-1.47 (m, 2H), 1.11-1.17 (m, 4H), 0.70-0.74 (m, 3H).

Example 6

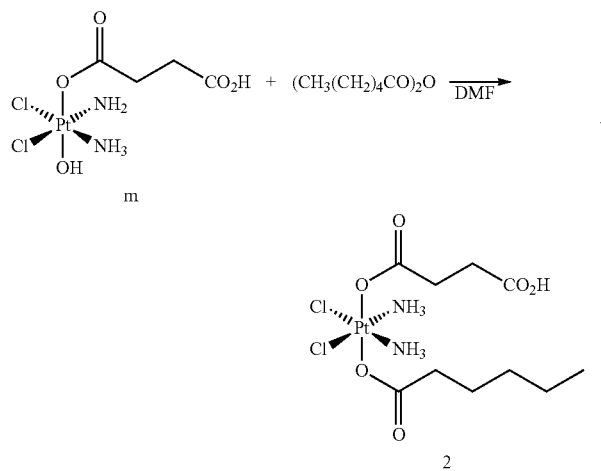

Platinum (IV) diamminedichlorosuccinate (983 mg, 2.26 mmol, prepared by using a procedure similar to Example 5) was dissolved in N,N-dimethylformamide (29 mL) and hexanoic anhydride (576 µL, 2.42 mmol) was added. The reaction was stirred for 16 h at ambient temperature. The solvent was removed under vacuum at 38° C. and the residue was co-evaporated with methanol (3×10 mL) to remove residual DMF. The residue was dissolved in methanol (2 mL) and the solution was added to tert-butylmethylether (25 mL) to give a white precipitate. The solution was spun-down using a centrifuge (500 rpm, 5° C.) and the supernatant decanted. The solid plug was re-suspended in tert-butylmethylether (20 mL) and spun-down again. The supernatant was removed and the plug suspended in tert-butylmethylether (20 mL). The suspension was filtered to give a white solid that was dried under high vacuum at 40° C., to yield 800 mg of product 2 (1.5 mmol, 67% yield). The product was analyzed by HPLC (method 2) and gave a peak retention time 1.4 minutes versus the starting material retention time 2.8 minutes.

Analysis by LCMS (Waters ZQ Micromass) gave a peak at 532 (MH$^+$). Characterization by 1HNMR (Varian 400 MHz) d$_6$-DMSO gave δ 6.5 (6H, b), δ 2.5 (2H, m), 2.2 (2H, t), 1.4 (2H, m), 1.2 (4H, m), 0.8 (3H, t).

Example 7

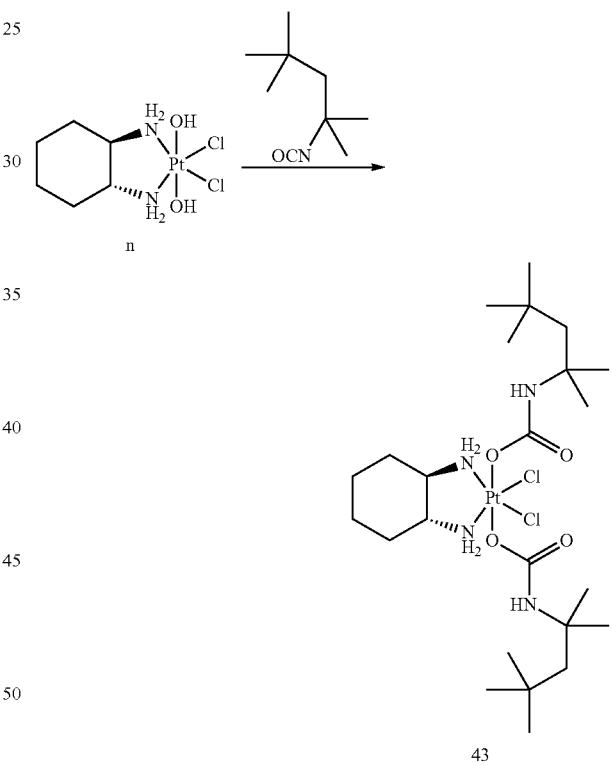

Dichloro[(1R,2R)-1,2-cyclohexanediamine-κN,κN']dihydroxyplatinum (n) (5.00 g, 12.1 mmol) was suspended in N,N-dimethylformamide (75 mL) and 2-isocyanato-2,4,4-trimethylpentane (5.60 g, 36.1 mmol, 3.00 equiv.) was added. The solution was stirred at 40° C. for 5 days. The solution was centrifuged and then decanted. 2.00 g of unreacted starting material was recovered from the decanted solid. The solvent from the filtrate was removed under vacuum and the crude residue was purified on silica gel chromatography (gradient elution 20-50% ethyl acetate in heptane) to afford 3.00 g (34%) of 43. LCMS retention time: 2.271 minutes; MH$^+$ 723.0, 724.0, 724.9, 726.0, 727.0.

Example 8

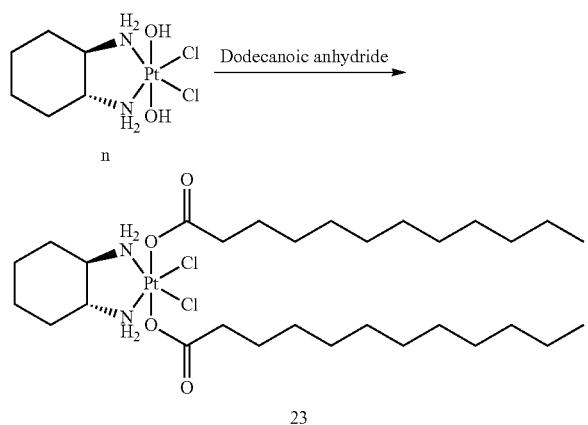

Compound n (200 mg, 0.483 mmol) was suspended in dimethylsulfoxide (5 mL) and dodecanoic anhydride (932 mg, 2.41 mmol, 5.00 equiv.) was added. The solution was stirred at 40° C. for 16 h. The solvent was removed under vacuum and the crude residue was purified on preparative HPLC (acetonitrile/water) to afford 20 mg (5%) of compound 23. LCMS retention time: 1.847 minutes; $MH^+$ 776.7, 777.8, 778.7, 779.7, 780.7.

Example 9

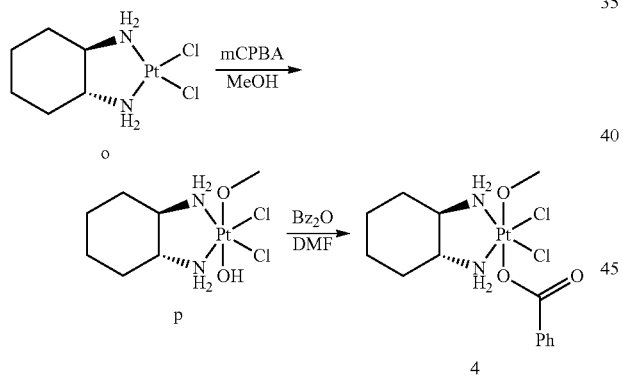

Synthesis of Compound 4

Step 1:
Dichloro[(1R,2R)-1,2-cyclohexanediamine-κN¹,κN²] platinum (o) (380 mg, 1.00 mmol) was weighed in a 25 mL round bottom flask and suspended in 5 mL of anhydrous MeOH. The solution was sonicated to provide a fine suspension and mCPBA (344 mg, 2.00 mmol, 2.00 equiv.) was then added. The reaction mixture was stirred at room temperature for 5 minutes. A precipitate formed and was filtered and dried to afford 90 mg. TBME (20 mL) was added onto filtrate, which caused more solid to precipitate. The solid was filtered then dried to afford 190 mg. Two solid crops of p were combined and used without further purification (280 mg).

Step 2:
Dichloro[(1R,2R)-1,2-cyclohexanediamine-κN,κN']hydroxy,methoxyplatinum (p) (150 mg, 0.350 mmol) was suspended in DMF (2 mL) and benzoic anhydride (158 mg, 0.700 mmol, 2.00 equiv.) was added. The solution was stirred at room temperature for 16 h. The solvent was removed under vacuum and crude residue was purified on preparative HPLC (acetonitrile/water) to afford 18 mg (10%) of compound 4. LCMS Rat 1.028 mins $MH^+$ 530.8, 531.8, 532.8, 533.8, 534.8.

Example 10

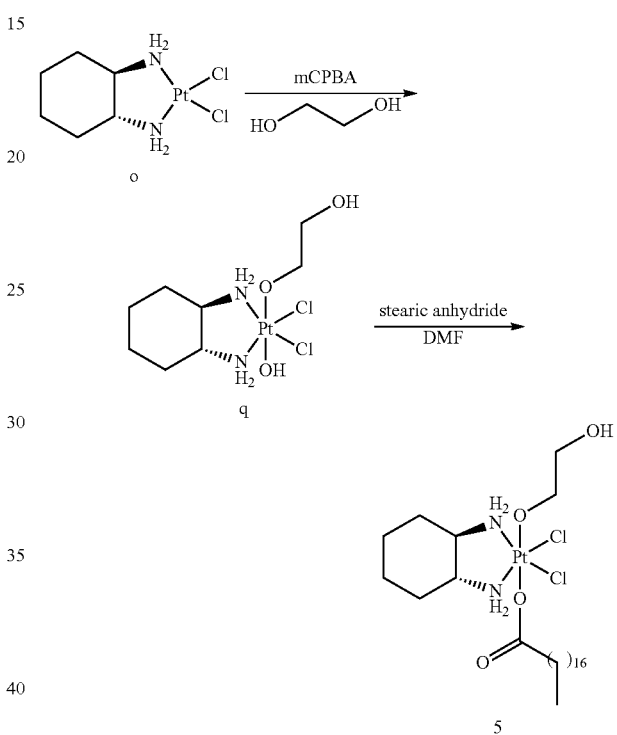

Synthesis of Compound 5

Step 1:
Dichloro[(1R,2R)-1,2-cyclohexanediamine-κN¹,κN²] platinum (o) (820 mg, 2.16 mmol) was weighed in a 25 mL round bottom flask and suspended in anhydrous ethylene glycol (4.0 mL). The solution was sonicated to provide a fine suspension and mCPBA (743 mg, 4.32 mmol, 2.00 equiv.) was then added. The reaction mixture was stirred at room temperature for 2 h. TBME (20 mL) was added, which caused solid to precipitate. The solid was filtered then dried to yield compound q (350 mg) which was used without further purification.

Step 2:
The crude dichloro[(1R,2R)-1,2-cyclohexanediamine-κN,κN']hydroxy, (2-hydroxyethoxy)platinum (q) (90 mg, 0.197 mmol) was suspended in DMF (2 mL) and stearic anhydride (218 mg, 554 0.393 mmol, 2.00 equiv.) was added. The solution was stirred at room temperature for 16 h. The solvent was removed under vacuum and crude residue was purified on preparative HPLC (acetonitrile/water) to afford 15 mg (15%) of compound 5. LCMS Rat 2.818 mins $MH^+$ 723.0, 724.0, 725.0.

The following analogs were prepared analogously to compounds 23 and 43 starting from dichloro[(1R,2R)-1,2-cyclohexanediamine-κN,κN']dihydroxyplatinum (n) by using the appropriate isocyanate or anhydride.

| Compound | Structure | Retention time (minutes)[a] | Mass |
|---|---|---|---|
| 41 | 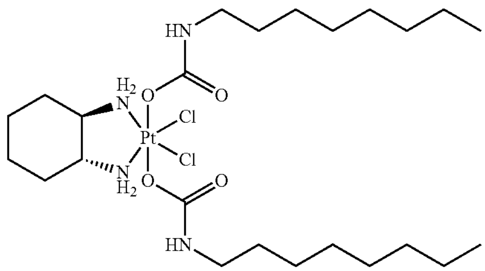 | 2.277 | 723.3, 724.3, 725.3, 726.3, 727.3 |
| 42 | 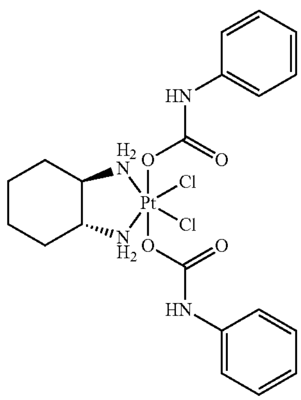 | 1.966 | 651.8, 652.7, 653.7, 654.8, 655.8 |
| 20 | 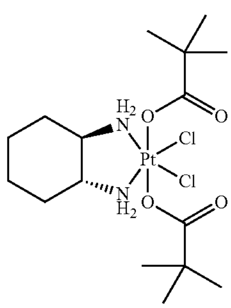 | 1.907 | 582.1, 583.2, 584.2, 585.2, 586.2 |
| 21 | 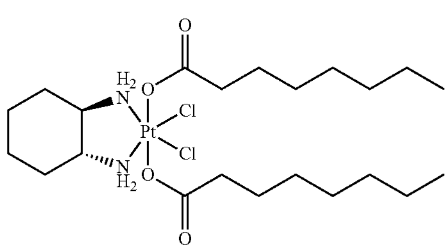 | 2.214 | 664.9, 665.9, 667.0, 668.0, 669.0 |

-continued

| Compound | Structure | Retention time (minutes)[a] | Mass |
|---|---|---|---|
| 24 | 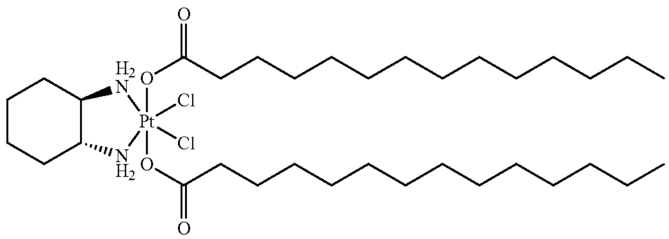 | 2.478 | 855.0, 856.0, 857.0, 858.0, 859.0, 860.0 |
| 22 | 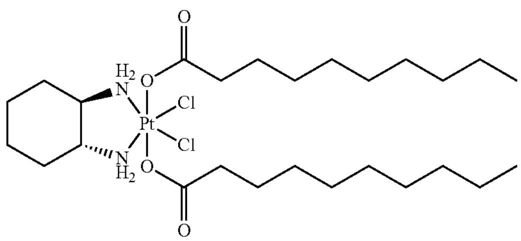 | 2.516 | 721.0, 722.0, 723.0 |
| 25 | 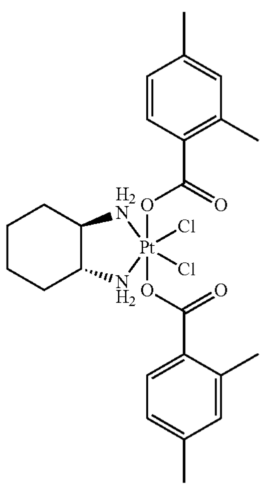 | 2.119 | 678.2, 679.2, 680.2 |
| 26 | 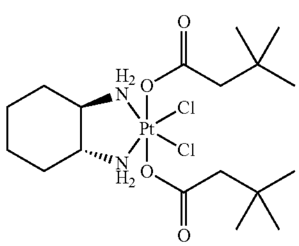 | 1.336 | 609.0, 610.0, 611.0, 612.0, 613.0 |

[a] HPLC/MS conditions: Mobile Phase: A: water (0.01% TFA) B: ACN (0.01% TFA); Gradient: 5%-95% B in 1.4 minutes; Flow Rate: 2.3 mL/min, 3.2 minute run; Column: SunFire C18, 4.6 × 50 mm, 3.5 μm; Oven Temperature: 50° C.

The following analogs were prepared analogously to compound 4 starting from dichloro[(1R,2R)-1,2-cyclohexanediamine-κN$^1$,κN$^2$] platinum by using the appropriate isocyanate or anhydride in step 2.

| Compound | Structure | Retention time (mins)[a] | Mass |
|---|---|---|---|
| 6 | 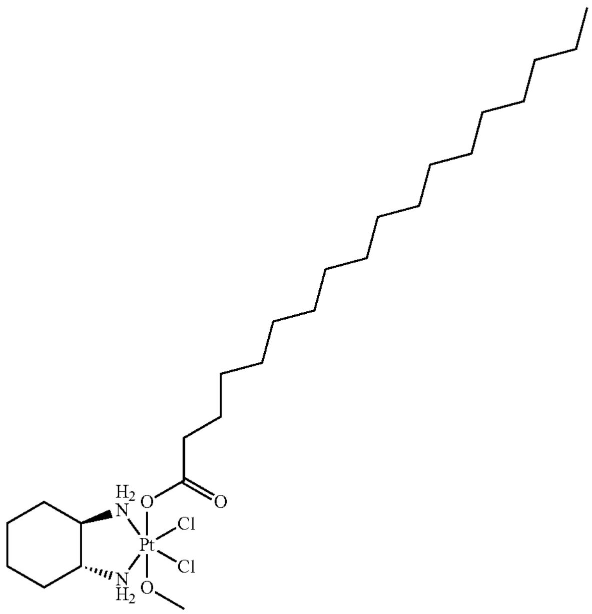 | 2.892 | 693.0, 694.0, 695.0 |
| 7 | 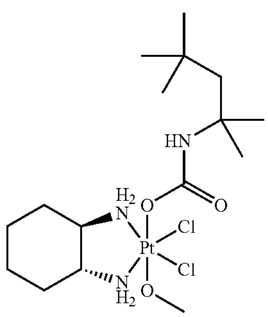 | 1.863 | 581.9, 582.8, 583.8, 584.8, 585.8 |

[a] HPLC/MS conditions: Mobile Phase: A: water (0.01% TFA) B: ACN (0.01% TFA); Gradient: 5%-95% B in 1.4 min; Flow Rate: 2.3 mL/min, 3.2 minute run; Column: SunFire C18, 4.6 × 50 mm, 3.5 μm; Oven Temperature: 50° C.

The following analogs were prepared analogously to compound 5 starting from dichloro[(1R,2R)-1,2-cyclohexanediamine-κN$^1$,κN$^2$] platinum by using the appropriate isocyanate or anhydride in step 2.

| Compound | Structure | Retention time (mins)[a] | Mass |
|---|---|---|---|
| 8 | 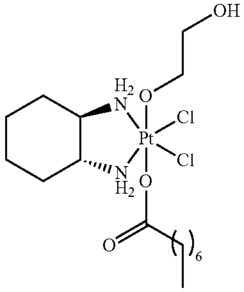 | 1.858 | 585.2, 586.2, 587.2, 588.2, 589.2 |

-continued

| Compound | Structure | Retention time (mins)[a] | Mass |
|---|---|---|---|
| 9 | 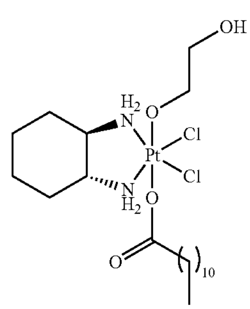 | 2.155 | 638.9, 639.9, 640.9, 641.9, 642.9 |

-continued

| Compound | Structure | Retention time (mins)[a] | Mass |
|---|---|---|---|
| 10 | (structure shown: Pt(IV) complex with cyclohexane diamine, two Cl, OH and long alkyl chain ester) | 2.321 | 669.2, 670.2, 671.2, 672.2, 673.2 |
| 11 | (structure shown: Pt(IV) complex with cyclohexane diamine, two Cl, OH and tert-butyl acetate ester) | 1.660 | 555.2, 556.2, 557.2, 558.2, 559.2 |

[a]HPLC/MS conditions: Mobile Phase: A: water (0.01% TFA) B: ACN (0.01% TFA); Gradient: 5%-95% B in 1.4 min; Flow Rate: 2.3 mL/min, 3.2 minute run; Column: SunFire C18, 4.6 × 50 mm, 3.5 µm; Oven Temperature: 50° C.

Example 11

Platinum(IV) Compounds Nanoparticle (NP)

Each of platinum(IV) compounds 29, 43, and 45 was successfully encapsulated in various polymers or polymer mixtures, representative examples of which are listed in tables below using (1) single oil in water emulsion, or (2) nanoprecipitation method. The polymer composition was varied by the ratio of the PLA or PLGA polymer to PLA-PEG or PLGA-PEG copolymer, as well as the PLA molecular weight (25-109 kDa). In process (1) the polymers and the drug were dissolved in ethyl acetate to achieve the desired active and total solids concentration. The oil phase was then slowly added to the continuously stirred aqueous phase containing an emulsifier (such as polysorbate 80 a.k.a. Tween® 80) at 10/90% or 20/80% v/v oil/water ratio and a coarse emulsion was prepared using a rotor-stator homogenizor or an ultrasound bath. The course emulsion was then processed through a high-pressure homogenizer (operated at 5,000 or 10,000 psi) for N=2 or 4 passes to form a nanoemulsion. In process (2) the polymers and the drug were dissolved in an organic solvent miscible with water (such as acetone) and added slowly to a continuously stirred aqueous phase with or without a stabilizer (such as polysorbate 80). In both processes (1) and (2) the nanoemulsion formed was quenched (by 5- or 10-fold dilution with cold (0-5° C.) or room temperature deionized water) to remove the major portion of the organic solvent resulting in hardening of the emulsion droplets and formation of a nanoparticle suspension, which was then concentrated and purified with deionized water containing or not surfactants using tangential flow filtration (500 kDa MWCO, mPES membranes).

Particle size (z-ave) and the polydispersity index (PDI) were characterized by dynamic light scattering, as summarized in the tables below. The actual drug load was determined gravimetrically by transferring 1 mL of the nanoparticle suspension to a 4 mL glass vial and drying under vacuum on a Rotavapor® to determine the amount of total remaining solids. The drug content was then determined by reconstituting the dried sample in an organic solvent (such as N'N'-dimethylformamide) and measuring the total amount of platinum using graphite furnace atomic adsorption spectroscopy (GF-AAS). Encapsulation efficiency was calculated as the ratio between the actual and the theoretical drug load. The yield was determined based on the ratio between the encapsulated and used compound amounts. In-vitro release was studied by incubating the nanoparticle suspension in phosphate buffered saline (PBS) containing a solubilizer such as 1% hydroxypropyl beta cyclodextrin for 24 h at 37° C. mixed continuously in a water shaking bath. Samples were taken at different time points and spun with an ultracentrifuge at 1,000,000×g to separate the nanoparticles from the dissolution medium. The supernatant was then analyzed using GF-AAS or HPLC to determine the active content as a function of time.

The formulations for in-vivo evaluation in a rat PK study were prepared by adding 10% w/w sucrose to the nanoparticle suspension. The formulations were stored frozen at ≤−20° C., and equilibrated at room temperature and sterile filtered through 0.22 um sterile filters prior the dosing. Dose verification samples were collected prior and post dosing and analyzed for potency to confirm the administered dose. Pharmacokinetic properties of the nanoparticles were studied by intravenous administration of 1 mg/kg compound 29, 43, or 45 to Sprague Dawley rats and taking bleeds over a 24 h period (n=3). The samples were analyzed by LC-MS/MS and ICP-MS to determine the concentration of compound 29, 43, or 45 and total platinum concentration correspondingly. Pharmacokinetic properties of compound 29, 43, or 45 dosed in solution or encapsulated in a nanoparticle are summarized in Table 1a, 1b, 2a, 2b, and 3 (ratio between the area under the curve for the nanoparticles and compound (6) solution ($AUC_{NP}/AUC_{solution}$) and FIGS. 1, 2, and 3. Accumulation in the tumor of Compound 29 and 43 encapsulated in a nanoparticle or as simple solution formulation was determined following an intravenous administration to tumor-bearing nude mice. The total platinum levels in the tumor determined by inductively coupled plasma mass spectrometry (ICP-MS) are given in FIGS. 4 and 5.

TABLE 1a

Platinum(IV) compound 29 nanoparticle in vitro and in vivo characterization

| | Formulation | | |
|---|---|---|---|
| | NP A | NP B | NP 1 |
| Polymers | 40% $PLA_{25}$/60% $PLA_{35}mPEG_5$ | 40% $PLA_{108}$/60% $PLA_{35}mPEG_5$ | 50% $PLA_{74}mPEG_5$/50% $PLA_{105}$ |
| Polymer Conc., mg/mL (Solvent) | 50 (ethyl acetate) | 50 (ethyl acetate) | 12.5 (acetone) |
| Process | Emulsion | Emulsion | Precipitation |
| Emulsifier/Stabilizer | 0.1% Tween 80 | 0.2% Tween 80 | 0.4% Tween 80 |
| Z-ave, PDI | 102, 0.05 | 104, 0.03 | 91, 0.1 |
| Target Drug Load (TDL), % | 10 | 10 | 10 |
| Actual Drug Load (ADL), % | 5.9 | 4.7 | 2.67 |

TABLE 1a-continued

Platinum(IV) compound 29 nanoparticle in vitro and in vivo characterization

| | Formulation | | |
|---|---|---|---|
| | NP A | NP B | NP 1 |
| EE % (ADL/TDL) | 59 | 47 | 27 |
| % Drug release at 4 h/24 h | NA | NA | NA |
| $AUC_{NP}/AUC_{Solution}$ | 43 | 61 | 268 |

NA—not available;
EE—encapsulation efficiency

TABLE 1b

Platinum(IV) compound 29 nanoparticle in vitro and in-vivo characterization

| | Formulation | | |
|---|---|---|---|
| | NP 2 | NP 3 | NP4 |
| Polymers | 50% $PLA_{74}mPEG_5$/ 50% $PLA_{105}$ | 50% $PLA_{74}mPEG_5$/ 50% $PLA_{105}$ | 50% $PLA_{15}mPEG_5$/ 50% $PLA_{105}$ |
| Polymer Conc., mg/mL (Solvent) | 200 (ethyl acetate) | 100 (ethyl acetate) | 100 (ethyl acetate) |
| Process | Emulsion | Emulsion | Emulsion |
| Emulsifier/Stabilizer | 0.8% Tween 80 | 0.4% Tween 80 | 0.4% Tween 80 |
| Z-ave, PDI | 129, 0.10 | 126, 0.12 | 95, 0.16 |
| Target Drug Load (TDL), % | 10 | 10 | 10 |
| Actual Drug Load (ADL), % | NA | 3.3 | 2.4 |
| EE % (ADL/TDL) | NA | 33 | 24 |
| % Drug release at 4 h/24 h | NA | 51/69 | 73/84 |
| $AUC_{NP}/AUC_{Solution}$ | 475 | NA | NA |

NA—not available;
EE—encapsulation efficiency

TABLE 2a

Platinum(IV) compound 43 nanoparticle in vitro and in-vivo characterization

| | Formulation | |
|---|---|---|
| | NP 1 | NP 2 |
| Polymers | 50% $PLA_{105}$/50% $PLA_{74}mPEG_5$ | 50% $PLA_{105}$/50% $PLA_{15}mPEG_5$ |
| Polymer Conc., mg/mL (Solvent) | 50 (ethyl acetate) | 100 (ethyl acetate) |
| Process | Emulsion | Emulsion |
| Emulsifier/Stabilizer | 0.2% Tween 80 | 0.5% DiHexPC |
| Z-ave, PDI | 105, 0.06 | 89, 0.28 |
| Target Drug Load (TDL), % | 5.3 | 4.8 |
| Actual Drug Load (ADL), % | 2.7 | 2.0 |
| EE % (ADL/TDL) | 44 | 43 |
| % Drug release at 2 h/24 h | 57.1/73.5 | NA |
| $AUC_{NP}/AUC_{Solution}$ | 585 | 69 |

NA—not available;
EE—encapsulation efficiency;
DiHexPC: 1,2-dihexanoyl-sn-glycero-3-phosphocholine
DiHepPC: 1,2-diheptanoyl-sn-glycero-3-phosphocholine;
PEG5000-DSPE: 1,2-dioleoyl-sn-glycero-3-phosphoethanolamine-N-[methoxy(polyethylene glycol)-5000] (ammonium salt)

TABLE 2b

Platinum(IV) compound 43 nanoparticle in vitro and in-vivo characterization

| | Formulation | |
|---|---|---|
| | NP 3 | NP 4 |
| Polymers | 100% $PLA_{35}mPEG_5$ | 50% $PLA_{105}$/50% $PLA_{15}mPEG_5$ |
| Polymer Conc., mg/mL (Solvent) | 100 (ethyl acetate) | 100 (ethyl acetate) |
| Process | Emulsion | Emulsion |
| Emulsifier/Stabilizer | 0.2% Tween 80 | 0.1% DiHepPC + PEG5000-DSPE |
| Z-ave, PDI | 104, 0.15 | 90, 0.20 |
| Target Drug Load (TDL), % | 5.6 | 5.6 |
| Actual Drug Load (ADL), % | 0.6 | 2.6 |
| EE % (ADL/TDL) | 12 | 46 |
| % Drug release at 2 h/24 h | NA | 61.4/89.7 |
| $AUC_{NP}/AUC_{Solution}$ | 15 | 135 |

NA—not available;
EE—encapsulation efficiency;
DiHexPC: 1,2-dihexanoyl-sn-glycero-3-phosphocholine
DiHepPC: 1,2-diheptanoyl-sn-glycero-3-phosphocholine;
PEG5000-DSPE: 1,2-dioleoyl-sn-glycero-3-phosphoethanolamine-N-[methoxy(polyethylene glycol)-5000] (ammonium salt)

TABLE 2c

Platinum(IV) compound 43 nanoparticle in vitro and in-vivo characterization

| | Formulation | | |
|---|---|---|---|
| | NP 5 | NP6 | NP7 |
| Polymers | 15% $PLA_{105}$/85% $PLA_{74}mPEG_5$ | 50% $PLA_{105}$/50% $PLA_{74}mPEG_5$ | 50% $PLA_{57}$/50% $PLA_{74}mPEG_5$ |
| Polymer Conc., mg/mL (solvent) | 100 (ethyl acetate) | 100 (ethyl acetate) | 80 (ethyl acetate) |
| Process | Emulsion | Emulsion | Emulsion |
| Emulsifier/Stabilizer | 0.5% Tween 80 | 0.5% Tween 80 | 0.5% DiHexPC |
| Z-ave, PDI | 100, 0.17 | 91, 0.14 | 110, 0.10 |
| Target Drug Load (TDL), % | 4.8 | 6.0 | 7.0 |
| Actual Drug Load (ADL), % | 1.3 | 1.5 | 2.9 |
| EE % (ADL/TDL) | 28 | 25 | 41 |
| % Drug release at 2 h/24 h | 52.2/84.8 | 55.0/91.5 | 31.8/81.4 |
| $AUC_{NP}/AUC_{Solution}$ | 376 | 595 | 655 |

NA—not available;
EE—encapsulation efficiency;
DiHexPC: 1,2-dihexanoyl-sn-glycero-3-phosphocholine
DiHepPC: 1,2-diheptanoyl-sn-glycero-3-phosphocholine;
PEG5000-DSPE: 1,2-dioleoyl-sn-glycero-3-phosphoethanolamine-N-[methoxy(polyethylene glycol)-5000] (ammonium salt)

TABLE 3

Platinum (IV) compound 45 nanoparticle in vitro and in-vivo characterization

| | Formulation NP A |
|---|---|
| Polymers | 15% $PLA_{25}$/85% $PLA_{74}mPEG_5$ |
| Polymer Conc., mg/mL (solvent) | 150 (ethyl acetate) |
| Process | Emulsion |
| Emulsifier/Stabilizer | None |
| Z-ave, PDI | 86, 0.26 |
| Target Drug Load (TDL), % | 7.2 |
| Actual Drug Load (ADL), % | 2.6 |
| EE % (ADL/TDL) | 36.7 |

TABLE 3-continued

Platinum (IV) compound 45 nanoparticle in vitro and in-vivo characterization

| | Formulation NP A |
|---|---|
| % Drug release at 4 h/24 h | NA |
| $AUC_{NP}/AUC_{Solution}$ | |

NA—not available;
EE—encapsulation efficiency

These data demonstrated that compounds 29, 43, and 45 can be incorporated into nanoparticles with an encapsulation efficiency between about 10% and about 60% and an actual drug load between about 0.6% and about 6%.

Example 12

Human cancer cell lines were plated in 96 well plates (Costar) and 24 hours later were treated with compound for 48-72 hours. Specifically, A549 cells (ATCC) were plated at 2,000 cells per well into white-walled clear bottomed 96 well plates and compound treatment was carried out for 72 hours. H460 cells (ATCC) were plated at a concentration of 1,500 cells per well and compound treatment was carried out for 48 hours. Compound starting dose was 20 µM and three fold serial dilutions were done for a total of ten points. Inhibition of proliferation was measured using Cell Titer Glo reagent using the standard protocol (Promega) and a Glomax multi+detection system (Promega). Percent proliferation inhibition was calculated using the following formula: % inhibition=(control−treatment)/control*100. Control is defined as vehicle alone. IC50 curves were generated using the nonlinear regression analysis (four parameter) with Graph Pad Prism 6.

Compounds of the present teachings each has an $IC_{50}$ value in a cell line (A549 CTG, HCT116, or H460) between 0.0001 µM and 50 µM. For example, as shown below, some examples of the present teachings each has an $IC_{50}$ value in a cell line (A549 CTG, HCT116, or H460) between 0.001 µM and 10 µM.

| Compound No. | $IC_{50}$/µM (cell line) |
|---|---|
| 4 | 0.36 (HCT116) |
| 5 | 0.018 (HCT116) |
| 6 | 0.021 (HCT116) |
| 7 | 0.275 (HCT116) |
| 8 | 0.388 (HCT116) |
| 9 | 0.116 (HCT116) |
| 10 | 0.021 (HCT116) |
| 11 | 2.53 (HCT116) |
| 20 | 0.034 (HCT116) |
| 21 | 0.0013 (HCT116) |
| 22 | <0.001 (HCT116) |
| 23 | 0.006 (HCT116) |
| 24 | 0.80 (HCT116) |
| 25 | 0.003 (HCT116) |
| 26 | 0.016 (HCT116) |
| 27 | 0.99 (A549) |
| 28 | 0.24 (A549) |
| 29 | 0.14 (A549) |
| 38 | 0.07 (A549) |
| 41 | 0.008 (HCT116) |
| 42 | 0.013 (H460) |
| 43 | 0.014 (HCT116) |
| 45 | 0.048 (A549) |

These data demonstrate that compounds described herein are efficacious for inducing cell death in a cancer cell.

Example 13

Rat Plasma PK Studies

Nanoparticles were typically formulated in 10% sucrose and free drug formulations varied, but were typically dosed in 10% Solutol®/10% sucrose, or physiological saline.

For PK studies, a 0.1 mg/mL solution was dosed at 10 mL/kg such that a 1 mg/kg IV bolus dose was introduced by tail vein injection. Following compound administration, blood was collected at 0.083 h, 0.25 h, 0.5 h, 1 h, 2 h, 4 h, 8 h, and 24 h post dose into lithium heparin coated vacuum tubes. Tubes were inverted for 5 minutes and then placed on wet ice until centrifuged for 5 minutes at 4° C. at 6000 rpm. Plasma was harvested, frozen at −80° C., and shipped on dry ice for bioanalysis.

Figure 2:
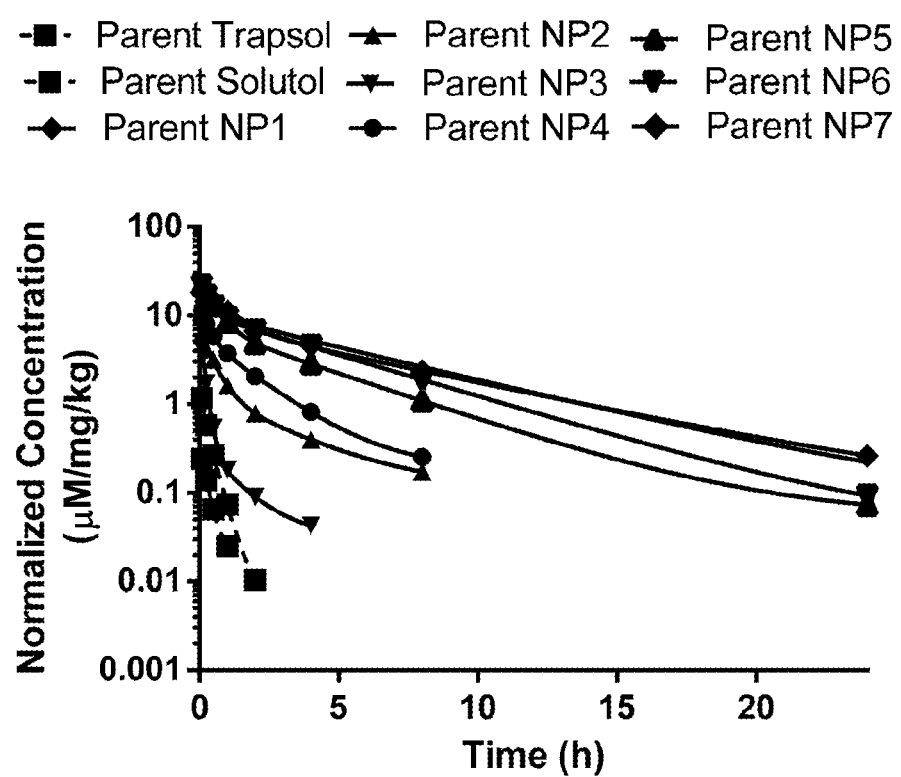
FIG. 2 shows exemplary rat plasma pharmacokinetic (pk) profiles of compound 43 administered as free drug and various exemplary nanoparticles.
Figure 3:
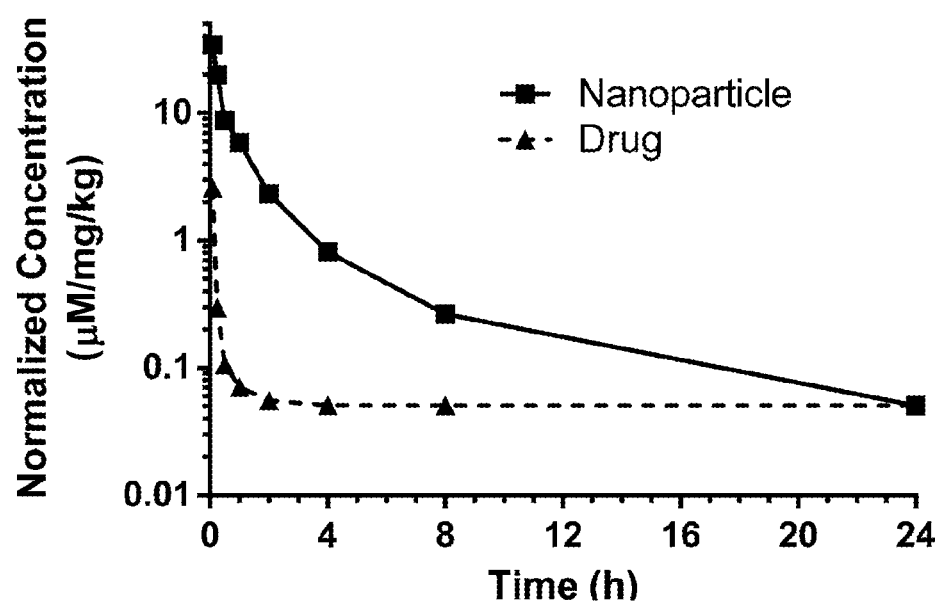
FIG. 3 shows exemplary rat plasma pharmacokinetic (pk) profiles of compound 45 administered as free drug and an exemplary nanoparticle.

50 uL of rat plasma were precipitated with 300 uL of DMF and the resulting supernatant was measured for the relevant compound by LC-MS/MS electrospray ionization in the positive mode. FIGS. 1, 2, and 3 show the plasma concentration of compound 29, 43, and 45, respectively, over time for the free compound and the various nanoparticle formulations.

These figures at least show that compounds of the present teachings maintain higher plasma concentrations when dosed as nanoparticles than as free compounds.

Example 14

Mouse PK/PD Studies

To examine the ability of compounds to accumulate in tumors, a murine cancer model was used. Animals were inoculated with $5 \times 10^5$ H460 small cell lung cancer cells via subcutaneous injection to the flank. Tumors were allowed to reach an approximate volume of ~500 mm$^3$. Animals were then randomized into treatment groups of 3 animals per time point and were dosed at 4 mg/kg. The 24 hour time point was used as a benchmark across compounds.

Tumor platinum levels were determined by inductively coupled plasma mass spectrometry (ICP-MS). Tumors were excised from animals and dissolved in fuming nitric acid (60% w/w) by adding four parts nitric acid to 1 part tumor w/w and heating overnight at 60 degrees Centigrade. The resulting digest was diluted 1:10 in ICP-MS analysis buffer (1% nitric acid, 2% Triton x-100), and directly introduced into the ICP-MS unit by peristaltic pump. The end dilution factor for the samples as introduced to the ICP-MS was 50×.

Figure 4:
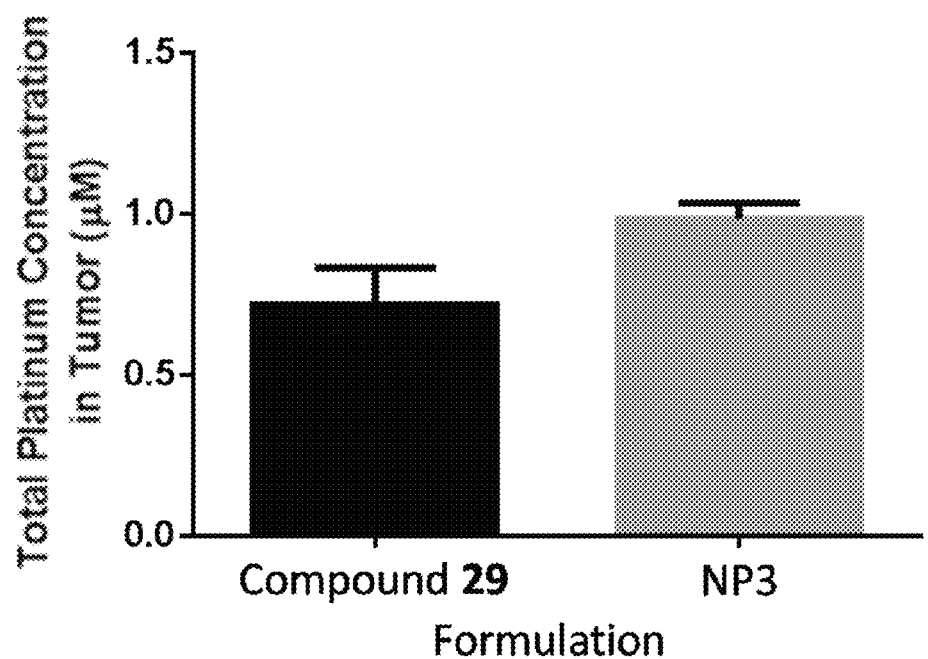
FIG. 4 shows exemplary platinum levels in tumor when compound 29 was dosed in a solution and a nanoparticle suspension, respectively, at 4 mg/kg to tumor-bearing nude mice via intravenous administration.
Figure 5:
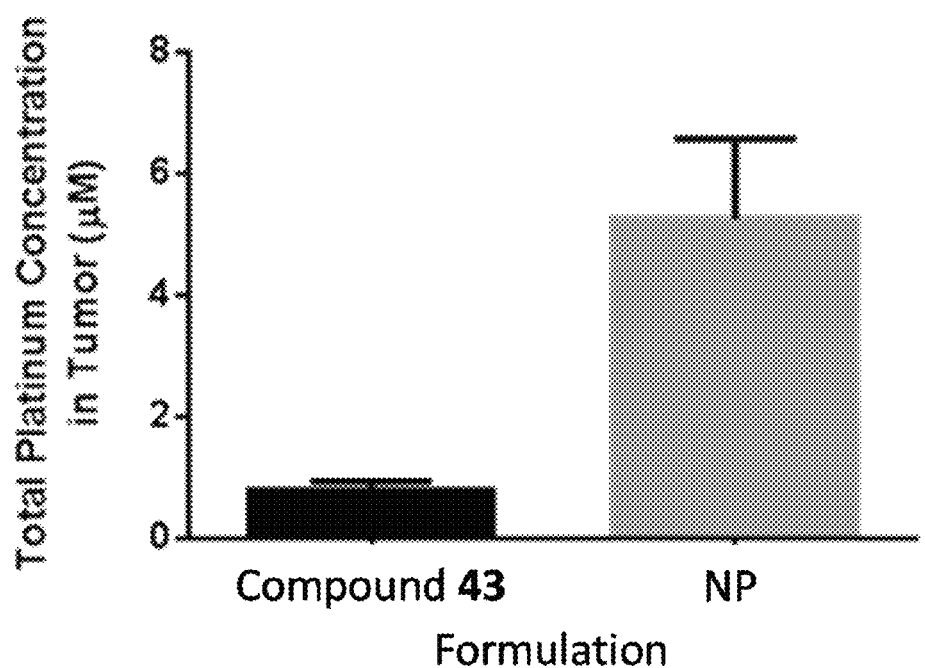
FIG. 5 shows exemplary platinum levels in tumor when compound 43 was dosed in a solution and a nanoparticle suspension, respectively, at 4 mg/kg to tumor-bearing nude mice via intravenous administration.

FIGS. 4 and 5 show the platinum levels in the tumor for compounds 29 and 43, respectively, in which each of the compounds was dosed as a free drug or formulated as a nanoparticle. Both the figures show higher platinum levels in the tumors when the corresponding compound was dosed as a nanoparticle suspension than as a free compound.

Example 15

The solubilities of the compounds in ethyl acetate (EA sol., mg/mL) in Table 4 were obtained. The maximum encapsulations (Max EE, %) and maximum drug load (Max DL, %) were obtained according to Example 11.

TABLE 4

| | EA sol., mg/mL | Max EE, % | Max DL, % |
|---|---|---|---|
| (structure 1) | <0.1 | | |
| (structure 2) | 2.0 | 2.8 | 0.55 |
| | 45 | 12.1 | 37 | 2.6 |
| | 29 | 57.6 | 59 | 5.9 |
| | 43 | 158 | 46 | 2.9 |

While several embodiments of the present teachings have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present teachings. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present teachings is/are used. Those skilled in the art will recognize, or be able to ascertain using no more than routine experimentation, many equivalents to the specific embodiments of the present teachings described herein. It is, therefore, to be understood that the foregoing embodiments are presented by way of example only and that, within the scope of the appended claims and equivalents thereto, the present teachings may be practiced otherwise than as specifically described and claimed. The present teachings are directed to each individual feature and/or method described herein. In addition, any combination of two or more such features and/or methods, if such features and/or methods are not mutually inconsistent, is included within the scope of the present teachings.

What is claimed is:

1. A compound selected from the group consisting of

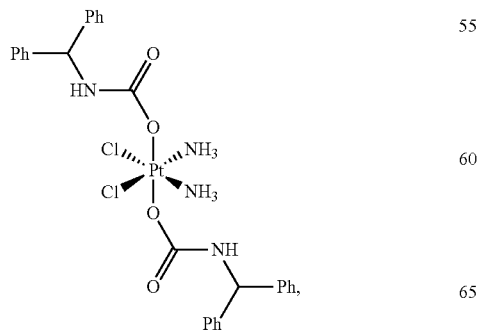

-continued

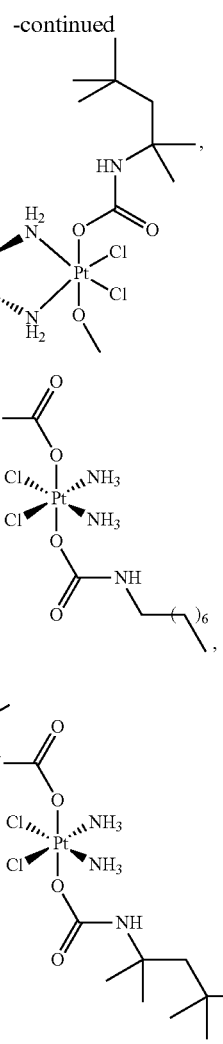

63
-continued
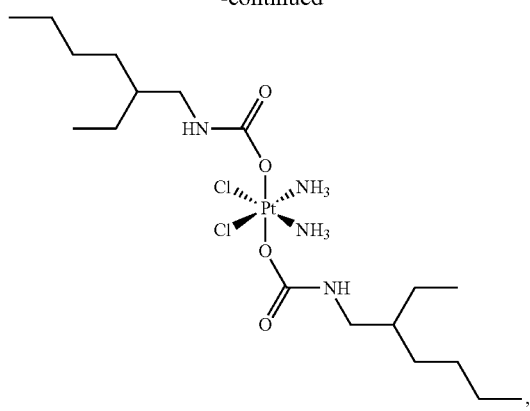
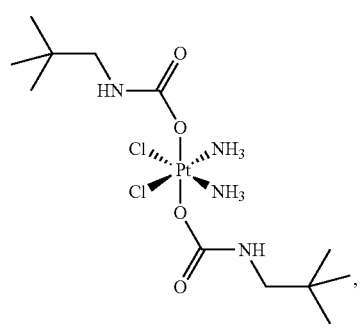
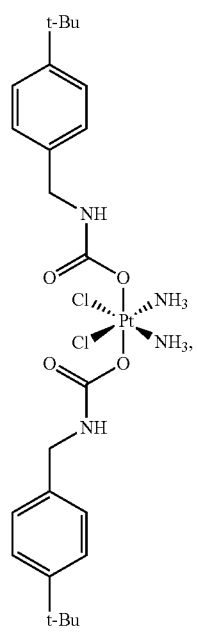
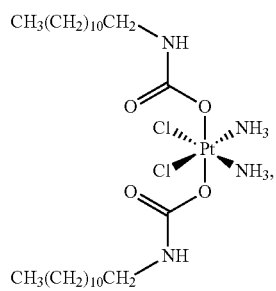
64
-continued
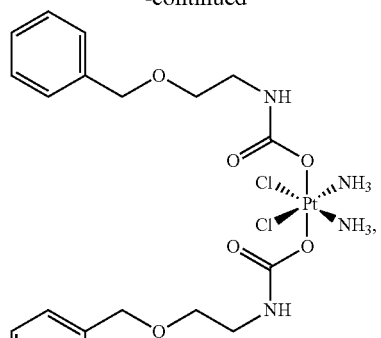
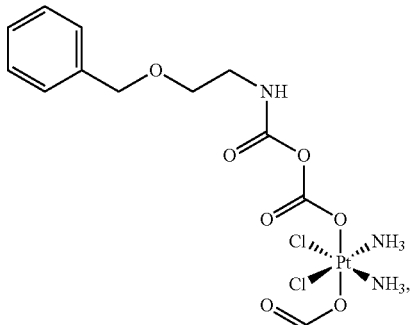
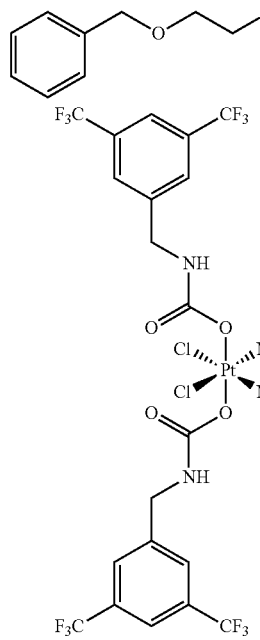
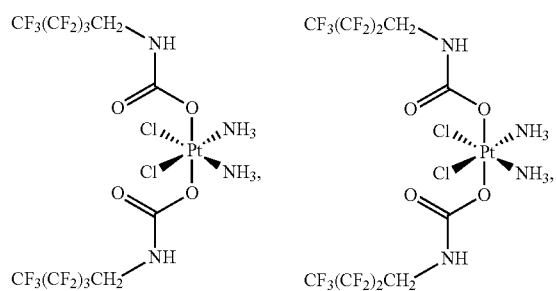

65
-continued
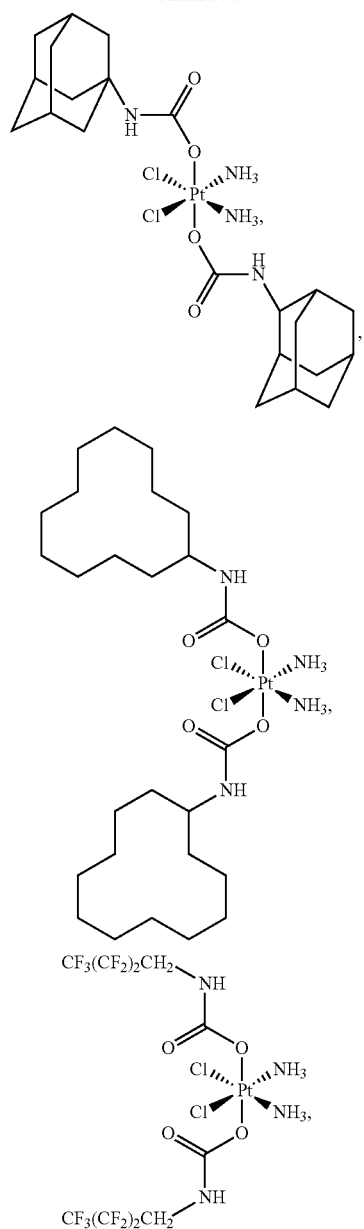
66
-continued
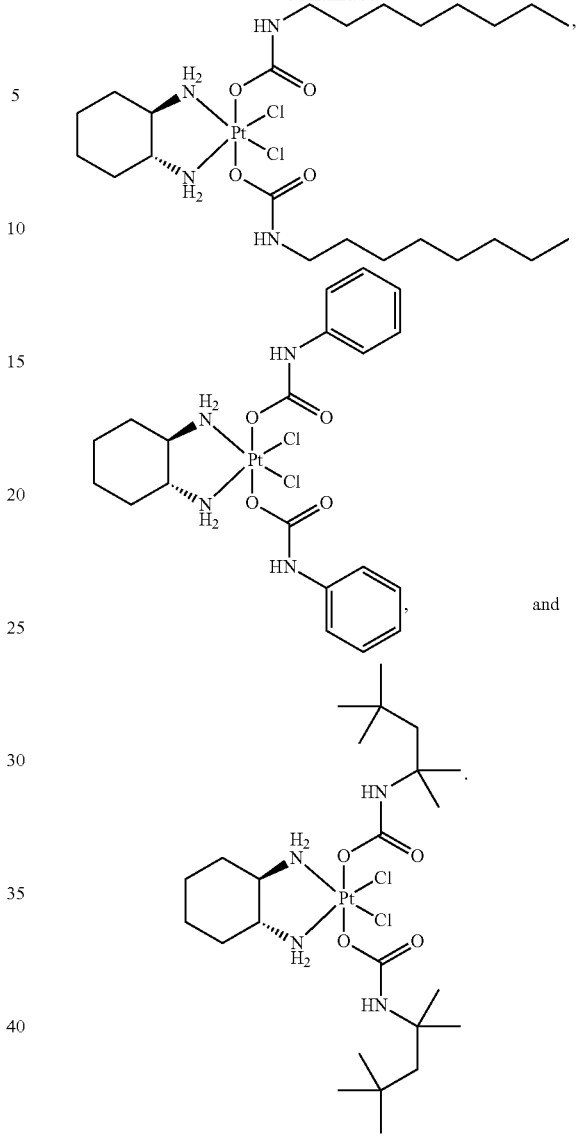
2. A pharmaceutical composition comprising a compound according to claim 1.
* * * * *